United States Patent [19]
Satoh et al.

[11] Patent Number: 5,541,182
[45] Date of Patent: Jul. 30, 1996

[54] BENZODIAZEPINE ARYL UREA DERIVATIVES

[75] Inventors: Masato Satoh; Yutaka Kondoh; Yoshinori Okamoto; Akito Nishida, all of Tsukuba; Kazuo Honda, Kawaguchi; Masayuki Saito, Tokyo, all of Japan

[73] Assignee: Yamanouchi Pharmaceutical Co., Ltd., Tokyo, Japan

[21] Appl. No.: 391,835

[22] Filed: Feb. 16, 1995

Related U.S. Application Data

[63] Continuation of Ser. No. 81,250, filed as PCT/JP91/01720 Dec. 17, 1991 published as WO92/11246, filed Sep. 7, 1992, abandoned.

[30] Foreign Application Priority Data

Dec. 25, 1990 [JP] Japan .................................. 2-418263
Feb. 20, 1991 [JP] Japan .................................. 3-111216
Oct. 2, 1991 [JP] Japan .................................. 3-282056

[51] Int. Cl.⁶ .................. A61K 31/55; C07D 243/24; C07D 243/26
[52] U.S. Cl. ................................. 514/221; 540/509
[58] Field of Search .......................... 540/509; 514/221

[56] References Cited

U.S. PATENT DOCUMENTS 4,820,834  4/1989  Evans ........................ 540/504

FOREIGN PATENT DOCUMENTS 0284256  3/1988  European Pat. Off. .
92-11246  7/1992  WIPO .

OTHER PUBLICATIONS

Noodruff, Neuropeptides 19, Snppl 45–56 (1991).

*Primary Examiner*—Mark L. Berch
*Attorney, Agent, or Firm*—Burgess, Ryan and Wayne

[57] ABSTRACT

This invention relates to novel benzodiazepine derivatives represented by the following general formula (I) or pharmaceutically acceptable salts thereof,

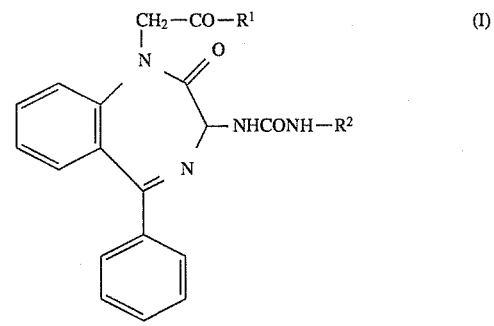

(wherein $R^1$ is an aryl group, or an aromatic heterocyclic radical of 5-membered monocyclic, 6-membered monocyclic or 5- and 6-membered bicyclic structure, which may optionally be substituted; and $R^2$ is an aryl group which may optionally be substituted), to medicinal compositions comprising the same, and to a process for producing the same. The compounds of formula (I) shown above exhibit antagonism for the CCK-B receptor and the action of depressing the gastric acid secretion caused by the stimulus of pentagastrin, and are therefore useful as a drug for the relief of diseases related to the CCK-B receptor and the gastrin receptor.

11 Claims, No Drawings

BENZODIAZEPINE ARYL UREA DERIVATIVES

This application is a continuation of application Ser. No. 08/081,250, filed as PCT/JP91/01720 Dec. 17, 1991 published as WO92/11246, filed Sep. 7, 1992, now abandoned.

TECHNICAL FIELD

This invention relates to novel benzodiazepine derivatives which are useful as a drug, particularly, as a drug exhibiting antagonism for the CCK-B receptor and/or the gastrin receptor, and to a process for producing the same.

BACKGROUND ART

Many investigations have hitherto been made on syntheses of benzodiazepine derivatives for the purpose of developing an agonist for the central nervous system acting upon the benzodiazepine receptor (a psychotropic drug).

It was recently reported that some of the benzodiazepine derivatives exhibit antagonism for the CCK-A (cholecystokinin-A) receptor and the CCK-B (cholecystokinin-B) receptor. It was also reported that the compounds exhibiting a higher degree of antagonism for the CCK-B receptor than that for the CCK-A receptor serve to depress the gastric-acid secretion caused by the stimulus of pentagastrin (Eur. J. Pharmacol., 162, 273–280, 1989).

DISCLOSURE OF THE INVENTION

In our studies on syntheses of benzodiazepine derivatives, the present inventors discovered novel benzodiazepine derivatives which are low in the affinity to the benzodiazepine receptor, do not show obvious action upon the central nervous system based on the benzodiazepine receptor, and exhibit a high degree of antagonism for the CCK-B receptor and/or the gastrin receptor. This invention was accomplished on the basis of this finding.

As the benzodiazepine derivatives exhibiting antagonism for the CCK-B receptor, are known those disclosed in U.S. Pat. No. 4,820,834. However, the compounds of this invention are novel derivatives which are clearly different from these compounds in chemical structure in terms of the substituent at the 1-position of benzodiazepine, and also in pharmacological action, exhibiting more potent and selective antagonism for the CCK-B receptor and/or the gastrin receptor (with a lower degree of antagonism for the benzodiazepine receptor and the CCK-A receptor).

This invention relates to novel benzodiazepine derivatives represented by the following general formula (I),

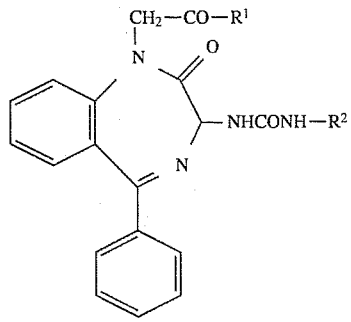

(wherein $R^1$ is an aryl group, or an aromatic heterocyclic radical of 5-membered monocyclic, 6-membered monocyclic or 5- and 6-membered bicyclic structure, which may optionally be substituted; and $R^2$ is an aryl group which may optionally be substituted).

The compounds of this invention are described below in more detail.

As examples of the "aryl group" in the above general formula (I), may be mentioned phenyl, indenyl and naphthyl groups, and these groups may optionally be substituted.

As examples of the substituent, may be mentioned lower alkyl groups, lower alkoxy groups and halogen atoms.

The lower alkyl group herein means a straight-chain or branched hydrocarbon radical with a carbon number of 1 to 6, its typical examples being methyl, ethyl, propyl, n-butyl, n-pentyl, isopropyl and sec-butyl groups; and the lower alkoxy group herein means the one having an above-mentioned lower alkyl group, such as methoxy, ethoxy, propoxy, isopropoxy and n-butoxy groups.

As examples of the halogen atom, may be mentioned fluorine, chlorine and bromine atoms.

As examples of the "aromatic heterocyclic ring of 5-membered monocyclic, 6-membered monocyclic or 5- and 6-membered bicyclic structure", may be mentioned thiophene, furan, pyrrole, thiazole, oxazole, imidazole, pyridine, benzothiophene, benzofuran and indole rings.

Each of the compounds of this invention, having an asymmetric carbon atom in the molecule, exists as optical isomers. In addition, the compounds of this invention form salts with inorganic and organic acids, and as examples of these salts, may be mentioned chlorides, sulfates and acetates.

PREPARATION METHOD

The compounds of this invention and salts thereof can be prepared by various synthesis methods utilizing their features based on the basic skeleton or on the type of substituents involved. Shown below is a typical preparation method.

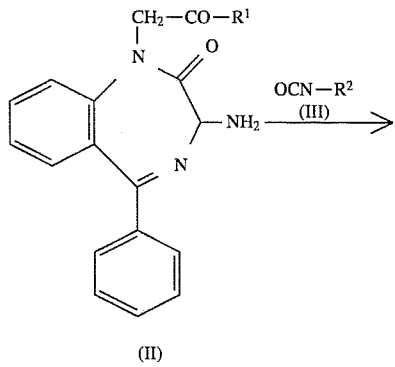

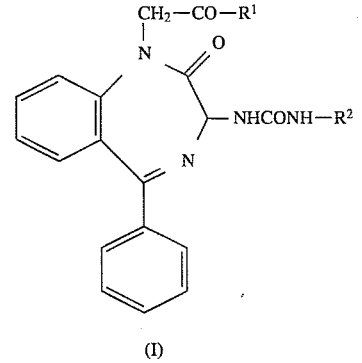

(wherein $R^1$ and $R^2$ are as defined above.)

The compounds of this invention (I) can be prepared by reaction of an amino compound represented by the general formula (II) with an isocyanate represented by the general formula (III). The isocyanate is generally used in an amount equimolar to that of the amino compound.

This reaction is carried out generally at room temperature in a solvent inert to the reaction, such as N,N-dimethylformamide, pyridine, benzene, toluene, dioxane, tetrahydrofuran, diethyl ether, chloroform, dichloromethane and n-hexane.

The reaction product formed can be isolated and purified by adopting ordinary operations, such as concentration, recrystallization and extraction. The reaction product can also be isolated in the form of various salts by using an equivalent or excessive amount of an acid.

INDUSTRIAL APPLICABILITY

The compounds of this invention exhibit potent and selective antagonism for the CCK-B receptor and the action of depressing the gastric-acid secretion caused by the stimulus of pentagastrin. Described below are these actions and the methods of measuring the same.

Measurement of the binding action upon CCK-B receptor:

About 100 heads of SD rats were decapitated without anesthesia, the whole brain was immediately excised from each of the cut heads and homogenized in 10-fold volume of 0.32M aqueous solution of sucrose by the use of a Teflon-coated homogenizer, the homogenate thus obtained was centrifuged for ten minutes at 900 g by the use of a cooled centrifuge, and the supernatant was further centrifuged for 15 minutes at 11500 g. The precipitate thus obtained was dispersed in 50 mM Tris-HCl buffer (pH 7.4) containing 0.08% Triton X-100, this suspension was allowed to stand for 30 minutes and again centrifuged for 15 minutes at 11500 g, the precipitate thus obtained was washed twice with 5 mM Tris-HCl buffer and twice with 50 mM Tris-HCl buffer in that order through centrifugal separation, the washed precipitate was suspended in 50 mM Tris-HCl buffer, and the suspension thus obtained was freeze-stored at −80° C., thus giving membrane preparation.

The membrane preparation was molten at room temperature, diluted with 10 mM HEPES buffer (containing 130 mM NaCl, 5 mM $MgCl_2$, 1 mM EGTA and 0.25 mg/ml bacitracin; pH 6.5) and incubated at 25° C. for 120 minutes in the presence of [$^{125}$I]BH•CCK-8, and B/F separation was performed by suction filtration. Nonspecific binding was determined in the presence of 1 μM CCK-8. The amount of labelled ligand bound to the receptor was measured by the use of a δ-counter; $K_i$(CCK-B) values were determined from the binding inhibition curve of the test sample, with the maximum amount of labelled ligand bound to the receptor being set as 100%.

$K_i$ values of the compounds of this invention were in the range from 0.03 to 10 nM as shown below.

|  | CCK-B binding Ki (nM) |
| --- | --- |
| Compound described in Example 281 of U.S. Pat. No. 4,820,834 | 29.0 |
| Compound of Example 2 | 0.15 |
| Compound of Example 7 | 0.22 |
| Compound of Example 13 | 0.16 |

Measurement of the action of depressing the gastric-acid secretion caused by the stimulus of pentagastrin:

A cannula was inserted into the trachea of a rat anesthetized with urethane (intraperitoneally administered in an amount of 1.25 g/kg), its abdominal wall was incised to expose the gastric and duodenal portions, and a polyethylene cannula was set at the anterior stomach after ligation of the cardia. The duodenum was then subjected to slight section, a polyethylene cannula was inserted from the incised portion toward the stomach, and the pylorus was ligated to fix the cannula.

Physiological saline (with pH adjusted to 7.0) was flown from the anterior stomach toward the pylorus at a speed of 3 ml/min, and the gastric-acid secretion was measured by continuous titration of the flown saline by the use of a pH-stat (AUT-201; product of Toa Electronics, Ltd.). The continuous titration was carried out by using 25 mM caustic soda solution until the pH reached 7.0, and the result was expressed as the amount of gastric acid secreted for every ten minutes ($\mu E_q$/10 min.). Pentagastrin was intravenously administered at a rate of 15 μg/kg/hr. The secretion of gastric acid increased upon administration of pentagastrin, reaching the maximum level after 60 minutes and stably maintaining this level after that. A test drug was then intravenously administered, and the secretion of gastric acid was measured, thereby obtaining the amount of the drug required to reduce the amount of secreted gastric acid down to 50% of the maximum level ($ED_{50}$). In this test, were used two kinds of animals (Wister rats and SD rats), and the result obtained with SD rats is shown below.

|  | Depression of gastric-acid secretion; $ED_{50}$ (μmol/kg) |
| --- | --- |
| Compound described in Example 281 of U.S. Pat. No. 4,820,834 | 4.2 |
| Compound of Example 2 | 0.030 |

Measurement of selectivity for CCK-B receptor by comparison with the binding to CCK-A receptor in rats:

The pancreas of an SD rat was homogenized in 20-fold volume of 50 mM Tris-HCl buffer (pH 7.7) by the use of a Polytrone-type homogenizer, the homogenate was twice centrifuged for 10 minutes at 50000 g by the use of an ultracentrifuge, the precipitate thus obtained was suspended in 40-fold volume of 50 mM Tris-HCl buffer (containing 0.2% BSA, 5 mM $MgCl_2$, 0.1 mg/ml bacitracin and 5 mM DTT; pH 7.7), and the suspension was freeze-stored at −80° C., thus giving membrane preparation.

The membrane preparation was then molten at room temperature, diluted ten times with the buffer and incubated at 37° C. for 30 minutes in the presence of [$^3$H]L-364, 718, and B/F separation was performed by suction filtration. Nonspecific binding was determined in the presence of 1 μM L- 364, 718. The amount of labelled ligand bound to the receptor was measured by the use of a liquid scintillation counter; $K_i$(CCK-A) values were determined from the binding inhibition curve of the test sample, with the maximum amount of labelled ligand bound to the receptor being set as 100%.

Side effects, such as cholestasis and gall stone formation, may occur when the antagonism for the CCK-A receptor is potent, and it is therefore preferable to be a selective antagonist for the CCK-B receptor.

The $K_i$(CCK-A)/$K_i$(CCK-B) value of the present compound can be calculated from the above test. The higher the value of $K_i$(CCK-A)/$K_i$(CCK-B), the higher will be the selectivity to the CCK-B receptor. It was demonstrated by the above test that the compounds of this invention exhibit the selectivity to CCK-B equal to, or higher than, the compound described in Example 281 of U.S. Pat. No. 4,820,834.

The compound described in Example 281 of U.S. Pat. No. 4,820,834 exhibited 186-fold selectivity for the CCK-B receptor. In contrast, the compounds of Example 2 and Example 7 of this invention exhibited selectivity to the CCK-B receptor as high as 1733-fold and 864-fold, respectively.

Binding to the benzodiazepine receptor

The binding action of the compounds of this invention to the benzodiazepine receptor is very weak. The compound described in Example 281 of U.S. Pat. No. 4,820,834 has an $IC_{50}$ value of 1.2 μM (Eur. J. Pharmacol., 162, 273–280, 1989), while the compound of Example 16 showed no binding action at all even at 10 μM.

The compounds of this invention are also low in toxicity and are suitable for use as a drug. In a test using SD rats, for example, no serious side effect was observed even when the compounds were orally administered in an amount of 100 mg/kg.

The above-described experiments demonstrated that the compounds of this invention exhibit the antagonism for the CCK-B receptor and the action of depressing the gastric-acid secretion caused by the stimulus of pentagastrin, and are therefore useful for the relief and prevention of diseases related to the CCK-B receptor and the gastrin receptor.

As examples of such diseases, may be mentioned digestive diseases, such as gastric ulcer, duodenal ulcer, gastritis, regurgitating esophagitis, Zollinger-Bllison syndrome and gastrin-sensitive pancreas; and the failure of the central nervous system, such as the failure of the appetite regulatory system, pains and anxiety.

The compounds of this invention and salts thereof are administered orally (including sublingual administration) or parenterally in the form of tablets, powders, fine granules, capsules, pills, liquids, injections, suppositories, ointments and adhesive plasters.

As the carrier and excipient for pharmaceutical manufacturing, is used a solid or liquid, nontoxic medicinal substance, such as lactose, magnesium stearate, starch, talc, gelatin, agar, pectin, gum arabic, olive oil, sesame oil, cacao butter, ethylene glycol and other commonly employed materials.

The clinical dosage of the compounds of this invention should be properly set depending on the illness conditions, body weight, age, sex and other factors of the patient to be treated, but is generally 1 to 1000 mg/day for adult when orally administered, which may be applied at a time or subdivided in several doses.

BEST FORM IN PRACTICING THE INVENTION

Described below are examples of pharmaceutical preparation using the compounds of this invention.

EXAMPLES OF TABLET PREPARATION

| Composition | 20 mg-Tablet (mg) | 40 mg-Tablet (mg) |
| --- | --- | --- |
| Compound of Example 16 | 20 | 40 |
| Lactose | 73.4 | 80 |
| Corn Starch | 18 | 20 |
| Hydroxypropylcellulose | 4 | 5 |
| Carboxymethylcellulose Ca | 4 | 4.2 |
| Mg Stearate | 0.6 | 0.8 |
| Total | 120 mg | 150 mg |

PREPARATION OF 20 mg-TABLETS

Compound of Example 16 (100 g), lactose (367 g) and corn starch (90 g) were homogeneously mixed together by the use of a flow granulating coater (product of Ohgawara Seisakusho), 10% aqueous solution of hydroxypropylcellulose (200 g) was sprayed to the mixture, and granulation was then performed. After drying, the granules were filtered through a 20-mesh sieve, 20 g of carboxymethylcellulose Ca and 3 g of magnesium stearate were then added, and the mixture was treated in a rotary tablet machine equipped with a pestle of 7 mm×8.4R (product of Hata Tekkosho), thus producing tablets each weighing 120 mg.

PREPARATION OF 40 mg-TABLETS

Compound of Example 16 (140 g), lactose (280 g) and corn starch (70 g) were homogeneously mixed together by the use of a flow granulating coater (product of Ohgawara Seisakusho), 10% aqueous solution of hydroxypropylcellulose (175 g) was sprayed to the mixture, and granulation was then performed. After drying, the granules were filtered through a 20-mesh sieve, 14.7 g of carboxymethylcellulose Ca and 2.8 g of magnesium stearate were then added, and the mixture was treated in a rotary tablet machine equipped with a pestle of 7.5 mm×9R (product of Hata Tekkosho), thus producing tablets each weighing 150 mg.

EXAMPLES

The following Examples will further illustrate the invention. With the novel compounds used as the starting materials in the Examples, their preparation methods are described in Reference Examples.

REFERENCE EXAMPLE 1

Starting material in Example 1

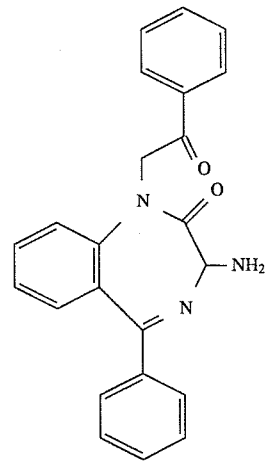

(a) To a mixture of 3.54 g 1,3-dihydro-5-phenyl-2H-1,4-benzodiazepin-2-one, 10.46 g phenacyl bromide, 0.15 ml tricaprylmethylammonium chloride and 60 ml toluene, was added a solution of 9 g caustic soda in 20 ml water under ice cooling, and the mixture was stirred at room temperature for six hours. After addition of 150 ml water, the reaction mixture was extracted twice with 100 ml toluene, the extract was washed twice with 100 ml water and then with saturated aqueous solution of sodium chloride, and then dried over anhydrous magnesium sulfate. The solvent was distilled off from the dried solution under reduced pressure, the residue was subjected to column chromatography on silica gel, and elution was conducted with a 1:2 mixture of ethyl acetate and n-hexane, giving 4.8 g of 1,3-dihydro-1-phenacyl-5-phenyl-2H-1,4-benzodiazepin-2-one.

PHYSICOCHEMICAL PROPERTIES

Melting point: 131°–133° C.

Mass spectrometric analysis, EI (m/z): 354 (M⁺)

NMR spectrum (CDCl$_3$; internal standard: TMS) δ: 3.95 (1H, d), 4.88 (1H, d), 5.14 (1H, d), 5.41 (1H, d), 7.1–8.1 (14H, m)

(b) To a mixture of 4.61 g 1,3-dihydro-1-phenacyl-2H-1,4-benzodiazepin-2-one, 3.65 g potassium tert-butoxide and 65 ml toluene, was added 2.1 ml isoamyl nitrite under cooling in an ice-methanol bath, and the mixture was stirred for two hours. The reaction mixture was added to a mixture of 130 ml ice water, 6.5 ml acetic acid and 130 ml ethyl acetate, the resulting mixture was stirred for one hour and subjected to liquid separation, the aqueous layer was extracted with 130 ml ethyl acetate, the two organic solutions were combined together, washed with water and with saturated aqueous solution of sodium chloride in that order and then dried over anhydrous magnesium sulfate, and the solvent was distilled off from the dried solution under reduced pressure. After subjecting the residue to azeotropic distillation together with toluene, 20 ml toluene was added, the resulting mixture was stirred for one hour under ice cooling, and the crystals which separated out were collected, thus giving 2.74 g of 1,3-dihydro-3-oxyimido-1-phenacyl-5-phenyl- 2H-1,4-benzodiazepin-2-one.

PHYSICOCHEMICAL PROPERTIES

Melting point: 209°–213° C.

Mass spectrometric analysis, EI (m/z): 383 (M⁺)

NMR spectrum (CDCl$_3$+DMSO-d$_6$; internal standard: TMS) δ: 5.25 (1H, d), 5.51 (1H, d), 7.0–8.1 (14H, m), 10.6 (1H, br)

(c) A mixture of 0.84 g 1,3-dihydro-3-oxyimido-1-phenacyl-5-phenyl- 2H-1,4-benzodiazepin-2-one, 0.21 g 5% ruthenium-carbon powder and 20 ml methanol was stirred overnight at 60° C. under an elevated hydrogen-gas pressure of 8 kg/cm². After filtering off the catalyst from the reaction mixture, the solvent was distilled off from the filtrate under reduced pressure, the residue was subjected to column chromatography on silica gel, and elution was conducted with a 30:1 mixture of chloroform and methanol, thus giving 0.76 g of 3-amino- 1,3-dihydro-1-phenacyl-5-phenyl-2H-1,4-benzodiazepin-2-one.

PHYSICOCHEMICAL PROPERTIES

Mass spectrometric analysis, EI(m/z): 369(M⁺)

NMR spectrum (CDCl$_3$; internal standard: TMS) δ: 2.46 (2H, br), 4.65 (1H, s), 5.33 (2H, s), 7.0–8.1 (14H, m)

REFERENCE EXAMPLE 2

Starting material in Example 2

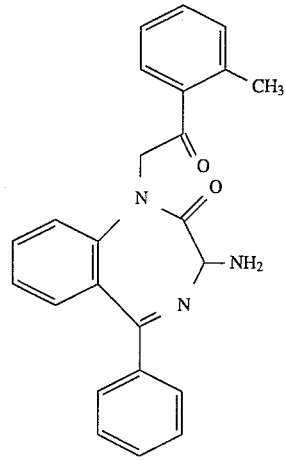

(a) To a mixture of 12.12 g 1,3-dihydro-5-phenyl-2H-1,4-benzodiazepin- 2-one, 16.40 g 2-bromo-2'-methylacetophenone, 0.27 g tricaprylmethylammonium chloride and 180 ml toluene, was added a solution of 29.55 g caustic soda in 60 ml water under ice cooling, and the mixture was stirred at room temperature for 1.5 hours. The aqueous layer was separated and extracted with 450 ml toluene, the two organic solutions were put together, and the combined solution was washed four times with 150 ml water and then with saturated aqueous solution of sodium chloride, and then dried over anhydrous magnesium sulfate. The solvent was distilled off from the dried solution, the residue was subjected to column chromatography on silica gel, elution was conducted with mixtures of ethyl acetate and n-hexane (3:2 to 1:1), and the eluted fractions thus obtained were subjected to recrystallization from a mixture of ethyl acetate and n-hexane, giving 14.78 g of 1,3-dihydro-1-(2'-methylphenacyl)- 5-phenyl-2H-1,4-benzodiazepin-2-one.

PHYSICOCHEMICAL PROPERTIES

Melting point: 119°–121° C.

Mass spectrometric analysis, EI(m/z): 368 (M⁺)

NMR spectrum (CDCl$_3$; internal standard: TMS) δ: 2.46 (3H, s), 3.93 (1H, d), 4.87 (1H, d), 5.14 (2H, d), 7.05–7.75 (13H, m)

(b) To a mixture of 14.70 g 1,3-dihydro-1-(2'-methylphenacyl)- 5-phenyl-2H-1,4-benzodiazepin-2-one and 205 ml toluene, was added 11.19 g potassium tert-butoxide at a temperature of −20° C., and the mixture was stirred for 20 minutes. Isoamyl nitrite (7.01 g) was then added dropwise over a period of 10 minutes, and the mixture was held at a temperature of −20° to −15° C. for 1.5 hours with stirring. The reaction mixture was added to a mixture of 410 g ice water, 20 ml acetic acid and 410 ml ethyl acetate, and the resulting mixture was stirred for one hour and subjected to liquid separation. The aqueous layer was extracted with 200 ml ethyl acetate, the two organic solutions were put together, and the combined solution was washed with water and with saturated aqueous solution of sodium chloride in that order, and then dried over anhydrous magnesium sulfate. The solvents were distilled off from the dried solution, and the residue was powdered by treatment with a mixture of ethyl acetate and n-hexane, giving 12.33 g of 1,3-dihydro-1-(2'-methylphenacyl)-3-oxyimido-5-phenyl-2H-1,4-benzodiazepin-2-one containing a small amount of the starting material. A part of this crude product was subjected to column chromatography on silica gel, the product obtained by elution with a 1:1 mixture of ethyl acetate and n-hexane was recrystallized from a mixture of ethyl acetate and n-hexane, thus giving the pure product.

PHYSICOCHEMICAL PROPERTIES

Melting point: 222°–227° C.

| Elemental analysis (as $C_{24}H_{19}N_3O_3$) | | | |
|---|---|---|---|
| | C (%) | H (%) | N (%) |
| Calcd. | 72.53 | 4.82 | 10.57 |
| Found | 72.37 | 4.91 | 10.32 |

Mass spectrometric analysis, EI(m/z): 397 ($M^+$)

NMR spectrum (DMSO; internal standard: TMS) δ: 2.33 (3H, s), 5.35 (2H, s), 7.10–7.90 (13H, m), 11.08 (1H, s)

(c) A mixture of 20.98 g 1,3-dihydro-1-(2'-methylphenacyl)-3-oxyimido-5-phenyl-2H-1,4-benzodiazepin-2-one, 4.20 g 5% ruthenium-carbon powder and 420 ml methanol was stirred at 60° C. for 23 hours under an elevated hydrogen-gas pressure of 8 kg/cm². After filtering off the catalyst from the reaction mixture, the solvent was distilled off from the filtrate. To the residue (19.07 g) thus obtained, were added 285 ml acetonitrile and a solution of 7.57 g (±)-mandelic acid in 100 ml acetonitrile in that order, the mixture was stirred at room temperature for one hour, and the crystals which separated out were collected by filtration and washed with 65 ml acetonitrile, giving 16.36 g of 3-amino-1,3-dihydro-1-(2'-methylphenacyl)- 5-phenyl-2H-1,4-benzodiazepin-2-one•mandelate.

PHYSICOCHEMICAL PROPERTIES

Melting point: 146°–150° C.

Mass spectrometric analysis, FAB, Pos(m/z): 384 ($M^++1$)

NMR spectrum (DMSO; internal standard: TMS) δ: 2.33 (3H, s), 4.64 (1H, s), 4.86 (1H, s), 5.35 (2H, s), 6.22 (4H, br), 7.23–7.85 (18H, m)

The mandelate thus obtained was treated with dichloromethane and 0.25N aqueous solution of caustic soda, thus giving free 3-amino-1,3-dihydro-1-(2'-methylphenacyl)-5-phenyl- 2H-1,4-benzodiazepin-2-one.

PHYSICOCHEMICAL PROPERTIES

Mass spectrometric analysis, FAB, Pos(m/z): 384 ($M^++1$)

NMR spectrum (CDCl₃; internal standard: TMS) δ: 2.10 (2H, br, s), 2.44 (3H, s), 4.62 (1H, s), 5.20 (2H, s), 7.10–7.69 (13H, m)

Compounds of Reference Examples 3 through 10 were obtained in the same way as in Reference Example 1 or 2.

REFERENCE EXAMPLE 3

Starting material in Example 3

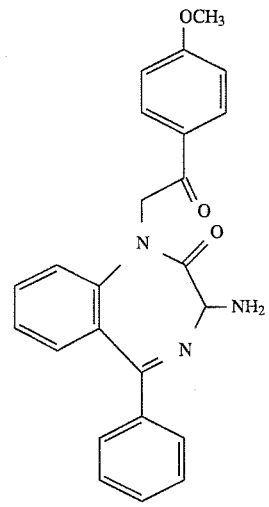

(a) Objective compound:
1,3-Dihydro-1-(4'-methoxyphenacyl)-5-phenyl-2H-1,4-benzodiazepin- 2-one
(b) Objective compound:
1,3-Dihydro-1-(4'-methoxyphenacyl)-3-oxyimido-5-phenyl- 2H-1,4-benzodiazepin-2-one
Starting material:
1,3-Dihydro-1-(4'-methoxyphenacyl)-5-phenyl-2H-1,4-benzodiazepin- 2-one
(c) Objective compound:
3-Amino-1,3-dihydro-1-(4'-methoxyphenacyl)-5-phenyl-2H-1,4-benzodiazepin-2-one
Starting material:
1,3-Dihydro-1-(4'-methoxyphenacyl)-3-oxyimido-5-phenyl- 2H-1,4-benzodiazepin-2-one

PHYSICOCHEMICAL PROPERTIES

Mass spectrometric analysis, EI (m/z): 399 ($M^+$)

NMR spectrum (CDCl₃; internal standard: TMS) δ: 3.74 (3H, s), 5.15 (1H, d), 5.29 (1H, s), 5.40 (1H, d), 6.81 (2H, d), 7.0–7.7 (9H, m), 7.84 (2H, m)

REFERENCE EXAMPLE 4

Starting material in Example 4

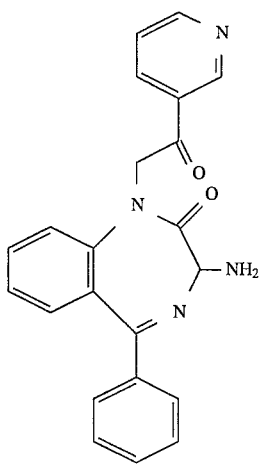

(a) 1,3-Dihydro-1-nicotinoylmethyl-5-phenyl-2H-1,4-benzodiazepin-2-one

PHYSICOCHEMICAL PROPERTIES

Melting point: 179°–181° C.

| Elemental analysis (as $C_{22}H_{17}N_3O_2$) | | | |
|---|---|---|---|
| | C (%) | H (%) | N (%) |
| Calcd. | 74.35 | 4.82 | 11.82 |
| Found | 74.47 | 4.78 | 11.65 |

(b) Objective compound:
  1,3-Dihydro-1-nicotinoylmethyl-3-oxyimido-5-phenyl-2H-1,4-benzodiazepin-2-one
  Starting material:
  1,3-Dihydro-1-nicotinoylmethyl-5-phenyl-2H-1,4-benzodiazepin-2-one
(c) Objective compound:
  3-Amino-1,3-dihydro-1-nicotinoylmethyl-5-phenyl-2H-1,4-benzodiazepin-2-one
  Starting material:
  1,3-Dihydro-1-nicotinoylmethyl-3-oxyimido-5-phenyl-2H-1,4-benzodiazepin-2-one

PHYSICOCHEMICAL PROPERTIES

Mass spectrometric analysis, EI(m/z): 370 (M⁺)

NMR spectrum (CDCl₃; internal standard: TMS) δ: 2.56 (2H, br), 4.67 (1H, s), 5.32 (2H, s), 7.0–7.8 (10H, m), 8.19 (1H, dt), 8.73 (1H, dd), 9.14 (1H, d)

REFERENCE EXAMPLE 5

Starting material in Example 5

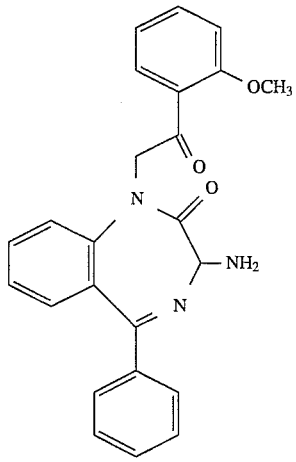

(a) Objective compound:
  1,3-Dihydro-1-(2'-methoxyphenacyl)-5-phenyl-2H-1,4-benzodiazepin-2-one
(b) Objective compound:
  1,3-Dihydro-1-(2'-methoxyphenacyl)-3-oxyimido-5-phenyl-2H-1,4-benzodiazepin-2-one
  Starting material:
  1,3-Dihydro-1-(2'-methoxyphenacyl)-5-phenyl-2H-1,4-benzodiazepin-2-one
(c) Objective compound:
  3-Amino-1,3-dihydro-1-(2'-methoxyphenacyl)-5-phenyl-2H-1,4-benzodiazepin-2-one
  Starting material:
  1,3-Dihydro-1-(2'-methoxyphenacyl)-3-oxyimido-5-phenyl-2H-1,4-benzodiazepin-2-one

PHYSICOCHEMICAL PROPERTIES

Mass spectrometric analysis, EI (m/z): 399 (M⁺)

NMR spectrum (CDCl₃; internal standard: TMS) δ: 3.90 (3H, s), 4.63 (1H, s), 5.11 (1H, d), 5.38 (1H, d), 6.80–8.0 (13H, m)

REFERENCE EXAMPLE 6

Starting material in Example 6

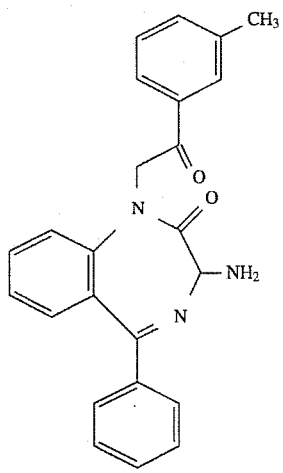

(a) Objective compound:
  1,3-Dihydro-1-(3'-methylphenacyl)-5-phenyl-2H-1,4-benzodiazepin- 2-one
(b) Objective compound:
  1,3-Dihydro-1-(3'-methylphenacyl)-3-oxyimido-5-phenyl- 2H-1,4-benzodiazepin-2-one
  Starting material:
  1,3-Dihydro-1-(3'-methylphenacyl)-5-phenyl-2H-1,4-benzodiazepin- 2-one
(c) Objective compound:
  3-Amino-1,3-dihydro-1-(3'-methylphenacyl)-5-phenyl-2H-1,4-benzodiazepin-2-one
  Starting material:
  1,3-Dihydro-1-(3'-methylphenacyl)-3-oxyimido-5-phenyl- 2H-1,4-benzodiazepin-2-one

PHYSICOCHEMICAL PROPERTIES

Mass spectrometric analysis, FAB, Pos(m/z): 384 (M⁺+1)

NMR spectrum (CDCl₃; internal standard: TMS) δ: 2.12 (2H, br, s)., 2.31 (3H, s), 4.62 (1H, s), 5.30 (2H, s), 7.08–7.78 (13H, m)

REFERENCE EXAMPLE 7

Starting material in Example 7

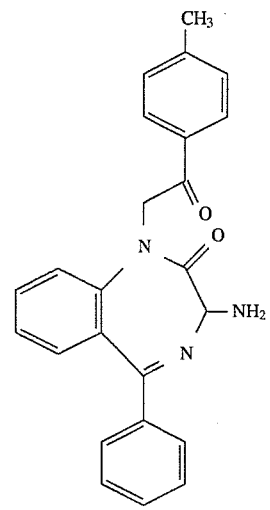

(a) Objective compound:
  1,3-Dihydro-1-(4'-methylphenacyl)-5-phenyl-2H-1,4-benzodiazepin- 2-one

PHYSICOCHEMICAL PROPERTIES

Mass spectrometric analysis, EI(m/z): 368 (M⁺)

NMR spectrum (CDCl₃; internal standard: TMS) δ: 2.33 (3H, s), 3.93 (1H, d), 4.88 (1H, d), 5.26 (2H, d), 7.06–7.85 (13H, m)
(b) Objective compound:
  1,3-Dihydro-1-(4'-methylphenacyl)-3-oxyimido-5-phenyl- 2H-1,4-benzodiazepin-2-one
  Starting material:
  1,3-Dihydro-1-(4'-methylphenacyl)-5-phenyl-2H-1,4-benzodiazepin- 2-one

PHYSICOCHEMICAL PROPERTIES

Melting point: 221°–224° C.

| | Elemental analysis (as C₂₄H₁₉N₃O₃) | | |
|---|---|---|---|
| | C (%) | H (%) | N (%) |
| Calcd. | 72.53 | 4.82 | 10.57 |
| Found | 72.45 | 4.91 | 10.39 |

Mass spectrometric analysis, EI(m/z): 397 (M⁺)

NMR spectrum (DMSO; internal standard: TMS) δ: 2.36 (3H, s), 5.52 (2H, d), 7.24–7.94 (13H, m) , 11.07 (1H, s)
(c) Objective compound:
  3-Amino-1,3-dihydro-1-(4'-methylphenacyl)-5-phenyl-2H-1,4-benzodiazepin-2-one
  Starting material:
  1,3-Dihydro-1-(4'-methylphenacyl)-3-oxyimido-5-phenyl- 2H-1,4-benzodiazepin-2-one

PHYSICOCHEMICAL PROPERTIES

Mass spectrometric analysis, FAB, Pos(m/z): 384 (M⁺+1)

NMR spectrum (CDCl$_3$; internal standard: TMS) δ: 2.00 (2H, br, s), 2.34 (3H, s), 4.66 (1H, s), 5.34 (2H, s), 7.16–7.88 (13H, m)

Mass spectrometric analysis, FAB, Pos (m/z): 384 (M⁺+1)

NMR spectrum (CDCl$_3$; internal standard: TMS) δ: 2.00 (2H, br, s), 2.34 (3H, s), 4.66 (1H, s), 5.34 (2H, s), 7.16–7.88 (13H, m)

REFERENCE EXAMPLE 8

Starting material in Example 8

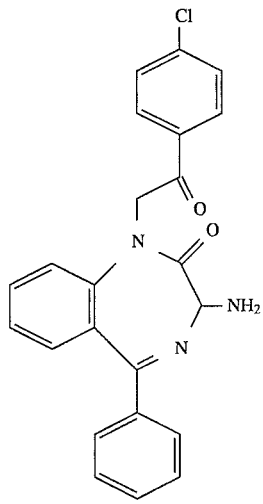

(a) Objective compound:
 1-(4'-Chlorophenacyl)-1,3-dihydro-5-phenyl-2H-1,4-benzodiazepin- 2-one
(b) Objective compound:
 1-(4'-Chlorophenacyl)-1,3-dihydro-3-oxyimido-5-phenyl- 2H-1,4-benzodiazepin-2-one
 Starting material:
 1-(4'-Chlorophenacyl)-1,3-dihydro-5-phenyl-2H-1,4-benzodiazepin- 2-one
(c) Objective compound:
 3-Amino-1-(4'-chlorophenacyl)-1,3-dihydro-5-phenyl-2H-1,4-benzodiazepin-2-one Starting material:
 1-(4'-Chlorophenacyl)-1,3-dihydro-3-oxyimido-5-phenyl- 2H-1,4-benzodiazepin-2-one

REFERENCE EXAMPLE 9

Starting material in Example 9

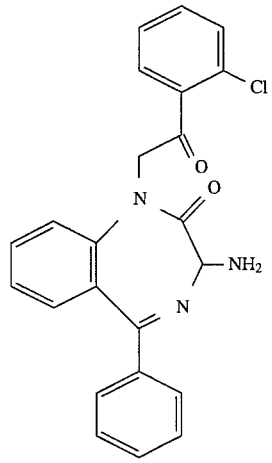

(a) Objective compound:
 1-(2'-Chlorophenacyl)-1,3-dihydro-5-phenyl-2H-1,4-benzodiazepin- 2-one
(b) Objective compound:
 1-(2'-Chlorophenacyl)-1,3-dihydro-3-oxyimido-5-phenyl- 2H-1,4-benzodiazepin-2-one
 Starting material:
 1-(2'-Chlorophenacyl)-1,3-dihydro-5-phenyl-2H-1,4-benzodiazepin- 2-one
(c) Objective compound:
 3-Amino-1-(2'-chlorophenacyl)-1,3-dihydro-5-phenyl-2H-1,4-benzodiazepin-2-one
 Starting material:
 1-(2'-Chlorophenacyl)-1,3-dihydro-3-oxyimido-5-phenyl- 2H-1,4-benzodiazepin-2-one

PHYSICOCHEMICAL PROPERTIES

Mass spectrometric analysis, EI(m/z): 403 (M⁺)

NMR spectrum (CDCl$_3$; internal standard: TMS) δ: 2.33 (2H, br), 4.62 (1H, s), 5.09 (1H, d), 5.28 (1H, d), 7.1–7.8 (13H, m)

REFERENCE EXAMPLE 10

Starting material in Example 10

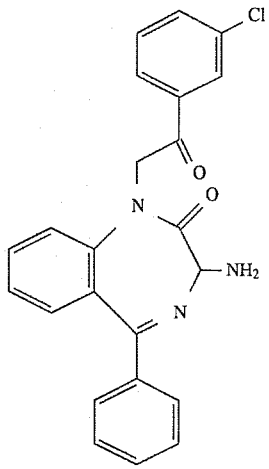

(a) Objective compound:

1-(3'-Chlorophenacyl)-1,3-dihydro-5-phenyl-2H-1,4-benzodiazepin- 2-one (b) Objective compound:

1-(3'-Chlorophenacyl)-1,3-dihydro-3-oxyimido-5-phenyl- 2H-1,4-benzodiazepin-2-one Starting material:

1-(3'-Chlorophenacyl)-1,3-dihydro-5-phenyl-2H-1,4-benzodiazepin- 2-one (c) Objective compound:

3-Amino-1-(3'-chlorophenacyl)-1,3-dihydro-5-phenyl-2H-1,4-benzodiazepin-2-one

Starting material:

1-(3'-Chlorophenacyl)-1,3-dihydro-3-oxyimido-5-phenyl- 2H-1,4-benzodiazepin-2-one

PHYSICOCHEMICAL PROPERTIES

Mass spectrometric analysis, EI (m/z): 403 (M$^+$)

NMR spectrum (CDCl$_3$; internal standard: TMS) δ: 2.85 (2H, br) , 4.70 (1H, s), 5.20 (1H, d), 5.43 (1H, d), 7.0–8.1 (13H, m)

REFERENCE EXAMPLE 11

Starting material in Example 11

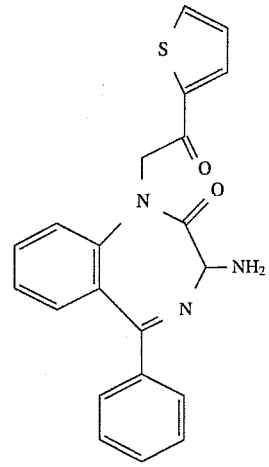

(a) To a mixture of 1.18 g 1,3-dihydro-5-phenyl-2H-1,4-benzodiazepin- 2-one, 3.6 g 2-bromoacetylthiophene, 0.05 ml tricaprylmethylammonium chloride and 20 ml toluene, was added 6 ml of 10N aqueous solution of caustic soda under ice cooling, and the mixture was stirred at room temperature for five hours. After addition of 100 ml water, the reaction mixture was extracted with toluene, the extract was washed with water and then with saturated aqueous solution of sodium chloride, and then dried over anhydrous magnesium sulfate. The solvent was distilled off from the dried solution under reduced pressure, the residue was subjected to column chromatography on silica gel, and elution was conducted with a 100:1 mixture of chloroform and methanol, giving 0.79 g of 1,3-dihydro-5-phenyl-1-(2-thenoyl)methyl-2H-1,4-benzodiazepin- 2-one.

PHYSICOCHEMICAL PROPERTIES

Mass spectrometric analysis, FAB, Pos(m/z): 361 (M$^+$+1)

NMR spectrum (CDCl$_3$; internal standard: TMS) δ: 3.94 (1H, d), 4.88 (1H, d), 5.11 (1H, d), 5.33 (1H, d), 6.9–7.9 (12H, m)

(b) To a mixture of 0.78 g 1,3-dihydro-5-phenyl-1-(2-thenoyl)methyl- 2H-1,4-benzodiazepin-2-one, 0.61 g potassium tert-butoxide and 11 ml toluene, was added 0.44 ml isoamyl nitrite under cooling in an ice-methanol bath, and the mixture was stirred for three hours. The reaction mixture was added to a mixture of 20 ml ice water, 1 ml acetic acid and 20 ml ethyl acetate, the resulting mixture was stirred for one hour and subjected to liquid separation, the aqueous layer was extracted with 20 ml ethyl acetate, the two organic solutions were put together, the combined solution was washed with water and with saturated aqueous solution of sodium chloride in that order and then dried over anhydrous magnesium sulfate, and the solvents were distilled off from the dried solution under reduced pressure. After subjecting the residue to azeotropic distillation together with toluene, 5 ml toluene was added, and the crystals which separated out were collected by filtration, thus giving 0.43 g of 1,3-dihydro- 3-oxyimido-5-phenyl-1-(2-thenoyl)methyl-2H-1,4-benzodiazepin- 2-one.

PHYSICOCHEMICAL PROPERTIES

Mass spectrometric analysis, EI(m/z): 389 (M$^+$)

NMR spectrum (DMSO-d$_6$; internal standard: TMS) δ: 5.27 (1H, d), 5.53 (1H, d), 7.0–8.3 (12H, m), 10.9 (1H, br)

(c) A mixture of 0.4 g 1,3-dihydro-3-oxyimido-5-phenyl-1-(2-thenoyl)methyl- 2H-1,4-benzodiazepin-2-one, 0.15 g 5% ruthenium-carbon powder and 15 ml methanol was stirred overnight at 60° C. under an elevated hydrogen-gas pressure of 8 kg/cm$^2$. After filtering off the catalyst from the reaction mixture, the solvent was distilled off from the filtrate under reduced pressure, the residue was subjected to column chromatography on silica gel, and elution was conducted with a 40:1 mixture of chloroform and methanol, thus giving 0.27 g of 3-amino-1,3-dihydro-5-phenyl-1-(2-thenoyl)methyl-2H-1,4-benzodiazepin-2-one.

PHYSICOCHEMICAL PROPERTIES

Mass spectrometric analysis, FAB, Pos(m/z): 376 (M$^+$+1)

NMR spectrum (CDCl$_3$; internal standard: TMS) δ: 3.0 (2H, br), 4.68 (1H, s), 5.25 (2H, s), 6.9–7.9 (12H, m)

REFERENCE EXAMPLE 12

Starting material in Example 12

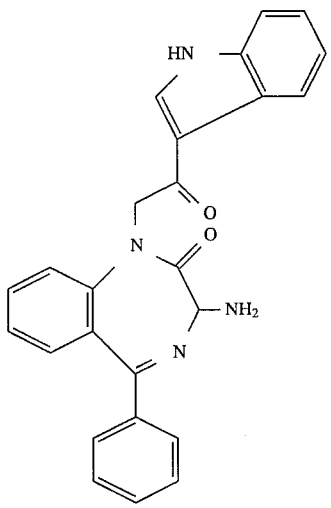

(a) A mixture of 1.18 g 1,3-dihydro-5-phenyl-2H-1,4-benzodiazepin- 2-one, 0.21 g sodium hydride and 25 ml N,N-dimethylformamide was stirred at room temperature for 30 minutes, 2.05 g 1-benzyloxycarbonyl-3-bromoacetylindole was then added gradually, and the resulting mixture was stirred at room temperature for three hours. The reaction mixture was ice-cooled, 100 ml water was added, the resulting mixture was extracted with a 2:1 mixture of ethyl acetate and toluene, and the extract was washed with water and with saturated aqueous solution of sodium chloride, and then dried over anhydrous magnesium sulfate. The solvents were distilled off from the dried solution under reduced pressure, the residue was subjected to column chromatography on silica gel, and elution was conducted with a 1:2 mixture of ethyl acetate and n-hexane, giving 1.4 g of 1-[(1-benzyloxycarbonyl- 3-indolylcarbonyl)methyl]-1,3-dihydro-5-phenyl- 2H-1,4-benzodiazepin-2-one.

PHYSICOCHEMICAL PROPERTIES

Mass spectrometric analysis, EI(m/z): 527 (M$^+$)

NMR spectrum (CDCl$_3$; internal standard: TMS) δ: 3.95 (1H, d), 4.90 (1H, d), 5.16 (2H, s), 5.37 (2H, s), 7.0–7.8 (16H, s), 8.0–8.4 (3H, m)

(b) To a mixture of 1.58 g 1-[(1-benzyloxycarbonyl-3-indolylcarbonyl)methyl]-1,3-dihydro-5-phenyl-2H-1,4-benzodiazepin- 2-one, 0.84 g potassium tert-butoxide and 15 ml toluene, was added 0.67 ml isoamyl nitrite under cooling in an ice-methanol bath, and the mixture was stirred for three hours. The reaction mixture was added to a mixture of 30 ml ice water, 1.5 ml acetic acid and 30 ml ethyl acetate, the resulting mixture was stirred for one hour and subjected to liquid separation, the aqueous layer was extracted with 30 ml ethyl acetate, the two organic solutions were put together, the combined solution was washed with water and with saturated aqueous solution of sodium chloride in that order and then dried over anhydrous magnesium sulfate, and the solvents were distilled off from the dried solution under reduced pressure. After subjecting the residue to azeotropic distillation together with toluene, 20 ml toluene was added, and the crystals which separated out were collected by filtration, thus giving 1.21 g of 1,3-dihydro-1-(3-indolylcarbonyl)methyl- 3-oxyimido-5-phenyl-2H-1,4-benzodiazepin-2-one.

PHYSICOCHEMICAL PROPERTIES

Mass spectrometric analysis, EI(m/z): 422 (M$^+$)

NMR spectrum (DMSO-d$_6$; internal standard: TMS) δ: 5.27 (1H, d), 5.51 (1H, d), 7.0–8.3 (13H, m), 11.03 (1H, s), 12.09 (1H, s)

(c) A mixture of 1.18 g 1,3-dihydro-1-(3-indolylcarbonyl)methyl- 3-oxyimido-5-phenyl-2H-1,4-benzodiazepin-2-one, 0.3 g 5% ruthenium-carbon powder and 23 ml methanol was stirred overnight at 60° C. under an elevated hydrogen-gas pressure of 8 kg/cm$^2$. After filtering off the catalyst from the reaction mixture, the solvent was distilled off from the filtrate under reduced pressure, the residue was subjected to column chromatography on silicon gel, and elution was conducted with a 20:1 mixture of chloroform and methanol, thus giving 0.38 g of 3-amino-1,3-dihydro-1-(3-indolylcarbonyl)methyl-5-phenyl- 2H-1,4-benzodiazepin-2-one.

PHYSICOCHEMICAL PROPERTIES

Mass spectrometric analysis, FAB, Pos(m/z): 409 (M$^+$+1)

NMR spectrum (DMSO-d$_6$; internal standard: TMS) δ: 3.23 (2H, br), 4.48 (1H, s), 5.17 (1H, d), 5.46 (1H, d), 7.0–7.8 (12H, m), 8.0–8.3 (1H, m), 8.43 (1H, s), 12.0 (1H, br)

The compound of Reference Examples 13 was obtained in the same way as in Reference Example 1 or 2.

REFERENCE EXAMPLE 13

Starting material in Example 13

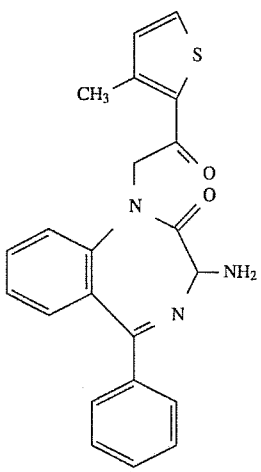

(a) Objective compound:
1,3-Dihydro-1-(3-methyl-2-thenoyl)methyl-5-phenyl-2H-1,4-benzodiazepin-2-one

PHYSICOCHEMICAL PROPERTIES

Mass spectrometric analysis, EI (m/z): 374 (M$^+$)

NMR spectrum (CDCl$_3$; internal standard: TMS) δ: 2.59 (3H, s), 3.59 (1H, d), 4.80 (1H, d), 4.88 (1H, d), 5.32 (1H, d), 6.97 (1H, d) , 7.0–7.8 (10H, m)

(b) Objective compound:
1,3-Dihydro-1-(3-methyl-2-thenoyl)methyl-3-oxyimido-5-phenyl-2H-1,4-benzodiazepin-2-one
Starting material:
1,3-Dihydro-1-(3-methyl-2-thenoyl)methyl-5-phenyl-2H-1,4-benzodiazepin-2-one

PHYSICOCHEMICAL PROPERTIES

Mass spectrometric analysis, EI(m/z): 403 (M$^+$)

NMR spectrum (DMSO-d$_6$; internal standard: TMS) δ: 2.49 (3H, s), 5.24 (2H, s), 7.0–8.0 (11H, m), 11.03 (1H, s), 6.97 (1H, d), 7.0–7.8 (10H, m)

(c) Objective compound:
3-Amino-1,3-dihydro-1-(3-methyl-2-thenoyl)methyl-5-phenyl- 2H-1,4-benzodiazepin-2-one
Starting material:
1,3-Dihydro-1-(3-methyl-2-thenoyl)methyl-3-oxyimido-5-phenyl-2H-1,4-benzodiazepin-2-one

PHYSICOCHEMICAL PROPERTIES

Mass spectrometric analysis, EI(m/z): 389 (M$^+$)

NMR spectrum (CDCl$_3$; internal standard: TMS) δ: 2.44 (2H, s), 2.57 (3H, s), 4.64 (1H, s), 4.89 (1H, d), 5.31 (1H, d), 6.96 (1H, d), 7.1–7.8 (10H, m)

REFERENCE EXAMPLE 14

Starting material in Example 14

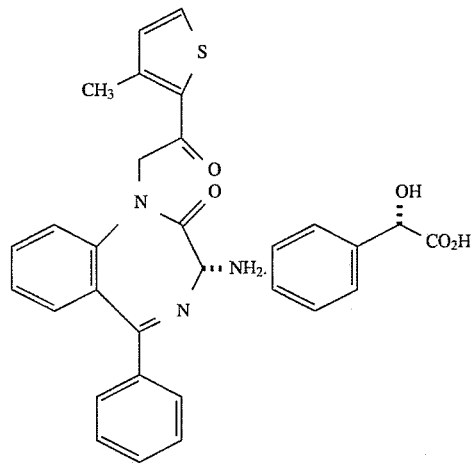

A mixture of 4.28 g 3-amino-1,3-dihydro-1-(3-methyl-2-thenoyl)methyl-5-phenyl-2H-1,4-benzodiazepin-2-one, 1.59 g (S)-mandelic acid, 63 mg 3,5-dichlorosalicylaldehyde and 110 ml acetonitrile was stirred at room temperature for three days. The crystals which separated out were collected by filtration and washed with 100 ml acetonitrile, thus giving 5.13 g of (R)-3-amino-1,3-dihydro-1-(3-methyl-2-thenoyl-)methyl- 5-phenyl-2H-1,4-benzodiazepin-2-one•(S)mandelate as white crystals.

PHYSICOCHEMICAL PROPERTIES i) $[\alpha]_D^{20}$=+170° C. (c=10, MeOH)
ii) Melting point: 179°–182° C.

| | iii) Elemental analysis (as $C_{30}H_{27}N_3O_3S$) | | | |
|---|---|---|---|---|
| | C(%) | H(%) | N(%) | S(%) |
| Calcd. | 66.53 | 5.02 | 7.76 | 5.92 |
| Found | 66.48 | 5.08 | 7.71 | 5.90 |

REFERENCE EXAMPLE 15

Starting material in Example 15

The following compound was obtained in the same way as in Reference Example 14.

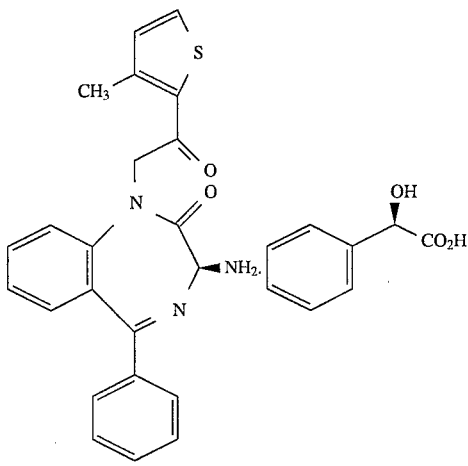

(S)-3-Amino-1,3-dihydro-1-(3-methyl-2-thenoyl)methyl-5-phenyl-2H-1,4-benzodiazepin-2-one•(R)-mandelate Starting material:

3-Amino-1,3-dihydro-1-(3-methyl-2-thenoyl)methyl-5-phenyl- 2H-1,4-benzodiazepin-2-one, and (R)-mandelic acid

PHYSICOCHEMICAL PROPERTIES i) $[\alpha]_D^{20} = -171°$ C. (c=10, MeOH)

ii) Melting point: 178°–181° C.

| iii) Elemental analysis (as $C_{30}H_{27}N_3O_3S$) | | | | |
| --- | --- | --- | --- | --- |
| | C(%) | H(%) | N(%) | S(%) |
| Calcd. | 66.53 | 5.02 | 7.76 | 5.92 |
| Found | 66.42 | 5.03 | 7.69 | 5.94 |

REFERENCE EXAMPLE 16

Starting materials in Examples 18 and 19

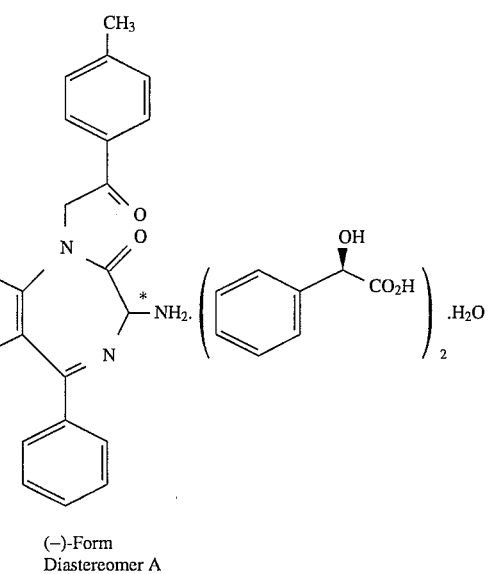

(−)-Form
Diastereomer A

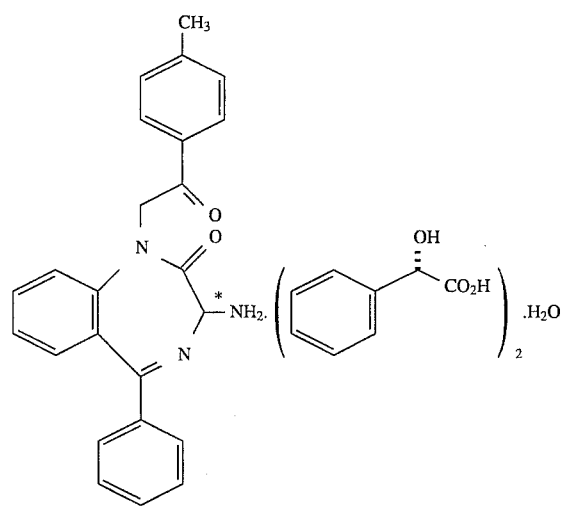

(+)-Form
Diastereomer B (a) To a mixture of 200 mg 3-amino-1,3-dihydro-1-(4'-methylphenacyl)- 5-phenyl-2H-1,4-benzodiazepin-2-one, 1.5 ml N,N-dimethylformamide and 116 mg N-(t-butoxycarbonyl)-D-phenylalanine, were added 172 mg diphenylphosphorylazide and 63 mg triethylamine, the mixture was stirred under ice cooling for one hour and then at room temperature overnight, 20 ml 10% aqueous solution of citric acid was then added, and the resulting mixture was extracted with 50 ml of a 2:1 mixture of ethyl acetate and toluene. The extract was washed with saturated aqueous solution of sodium bicarbonate, with water and with saturated aqueous solution of sodium chloride in that order, and then dried over anhydrous magnesium sulfate. The solvents were distilled off from the dried solution under reduced pressure, the residue was crystallized by addition of n-hexane, and the crystals were collected by filtration and washed with n-hexane, thus giving 324 mg of 1,1-dimethylethyl[(S)-2-[[2,3-dihydro-1-(4'-methylphenacyl)-5-phenyl- 2H-1,4-benzodiazepin-3-yl]amino]-2-oxo-1-(phenylmethyl)ethyl]carbamate.

PHYSICOCHEMICAL PROPERTIES

Mass spectrometric analysis, FAB, Pos(m/z): 631 ($M^+$+1)
NMR spectrum ($CDCl_3$; internal standard: TMS) δ: 1.40 (9H, s), 2.33 (3H, s), 3.00–3.30 (3H, m), 5.20–5.40 (2H, m), 5.59–5.62 (1H, m), 7.10–7.83 (20H, m)

(b) To 300 mg 1,1-dimethylethyl[(S)-2-[[2,3-dihydro-1-(4'-methylphenacyl)- 5-phenyl-2H-1,4-benzodiazepin-3-yl]amino]-2-oxo- 1-(phenylmethyl)ethyl]carbamate, was added 4N-HCl solution in ethyl acetate (1.2 ml) under ice cooling, and the mixture was stirred for one hour under ice cooling. The reaction mixture was adjusted to pH 9 by addition of 1N aqueous solution of caustic soda and extracted twice with 10 ml ethyl acetate, the extract was washed with water and with saturated aqueous solution of sodium chloride in that order an then dried over anhydrous magnesium sulfate, and the solvent was distilled off from the dried solution under reduced pressure. The residue was subjected to column chromatography on silica gel, and elution was conducted with ethyl acetate, thus giving 89 mg of 2(S)-amino-N-[2,3-dihydro- 1-(4'-methylphenacyl)-5-phenyl-2H-1,4-benzodiazepin- 3-yl]benzenepropaneamide diastereomer A ($R_f$ value: 0.58) (hereinafter referred to as Compound (b)-A) and 53 mg of diastereomer B ($R_f$ value: 0.45) (hereinafter referred to as Compound (b)-B).

PHYSICOCHEMICAL PROPERTIES

Compound (b)-A
Mass spectrometric analysis, FAB, Pos(m/z): 531 ($M^+$+1)
NMR spectrum ($CDCl_3$; internal standard: TMS) δ: 2.32 (3H, s), 2.82 (1H, dd), 3.38 (1H, dd), 3.71 (1H, dd), 5.28, 5.35 (each 1H, each d), 5.70 (1H, d), 7.10–7.90 (20H, m), 8.90 (1H, d)
$R_f$ value: 0.58 (developing solvent: ethyl acetate)

Compound (b)-B
Mass spectrometric analysis, FAB, Pos(m/z): 531 ($M^+$+1)
NMR spectrum ($CDCl_3$; internal standard: TMS) δ: 2.32 (3H, s), 3.70 (1H, dd), 3.37 (1H, dd), 3.75 (1H, dd), 5.26, 5.38 (each 1H, each d), 5.68 (1H, d), 7.10–7.90 (20H, m), 8.98 (1H, d)
$R_f$ value: 0.45 (developing solvent: ethyl acetate)

(c) To a mixture of Compound (b)-A obtained in the above step (b) (89 mg) and 0.5 ml dichloromethane, was added dropwise a mixture of 25 mg phenyl isothiocyanate and 0.5 ml dichloromethane, and the resulting mixture was stirred at room temperature for 15 hours. The solvent was distilled off from the reaction mixture, n-hexane was added to the residue, and the crystals which separated out were collected by filtration, thus giving 91 mg of 1-[[1-[2,3-dihydro-1-(4'-methylphenacyl)- 5-phenyl-2H-1,4-benzodiazepin-3-yl]-amino-1-oxo- 3-phenyl]prop-2(S)-yl]-3-phenylthiourea (Compound (c)-A).

Separately, the Compound (b)-B obtained in the above step (b) (53 mg) was also allowed to react in much the same manner as above, thus giving 60 mg of 1-[[1-[2,3-dihydro-1-(4'-methylphenacyl)-5-phenyl-2H-1,4-benzodiazepin-3-yl]amino-1-oxo-3-phenyl]prop-2(S)-yl]-3-phenylthiourea (Compound (c)-B).

PHYSICOCHEMICAL PROPERTIES

Compound (c)-A
Mass spectrometric analysis, FAB, Pos(m/z): 666 ($M^+$+1)
NMR spectrum ($CDCl_3$; internal standard: TMS) δ: 2.33 (3H, s), 3.34–3.45 (2H, m), 5.23, 5.34 (each 1H, each d), 5.41 (1H, m), 5.603 (1H, d), 6.80–8.00 (26H, m)

Compound (c)-B
Mass spectrometric analysis, FAB, Pos(m/z): 666 ($M^+$+1)
NMR spectrum ($CDCl_3$; internal standard: TMS) δ: 2.33 (3H, s), 3.35–3.42 (2H, m), 5.20, 5.37 (each 1H, each d), 5.37 (1H, m), 5.60 (1H, d), 6.80–7.95 (26H, m)

(d) To Compound (c)-A obtained above (83 mg), was added 0.15 ml trifluoroacetic acid, and the mixture was stirred at room temperature for three hours. The solvent was distilled off from the reaction mixture, the residue was subjected to column chromatography on silica gel, and elution was conducted with a 20:1 mixture of dichloromethane and methanol. The product thus eluted was dissolved in dichloromethane, this solution was washed with 1N aqueous solution of caustic soda and then with water, and dried over anhydrous magnesium sulfate, and the solvents were distilled off from the dried solution under reduced pressure, thus giving 29 mg of (+)-3-amino-1,3-dihydro-1-(4'-methylphenacyl)- 5-phenyl-2H-1,4-benzodiazepin-2-one (hereinafter referred to as Compound (d)-A).

Separately, the Compound (c)-B obtained in the above step (c) (60 mg) was also allowed to react in much the same manner as above, thus giving 19 mg of (−)-3-amino-1,3-dihydro- 1-(4'-methylphenacyl)-5-phenyl-2H-1,4-benzodiazepin- 2-one (hereinafter referred to as Compound (d)-B).

PHYSICOCHEMICAL PROPERTIES

Compound (d)-A
Mass spectrometric analysis, FAB, Pos(m/z): 384 ($M^+$+1)
NMR spectrum ($CDCl_3$; internal standard: TMS) δ: 2.33 (3H, s), 4.63 (1H, s), 5.31 (2H, s), 7.14–7.84 (13H, m)

Compound (d)-B
Mass spectrometric analysis, FAB, Pos(m/z): 384 ($M^+$+1)
NMR spectrum ($CDCl_3$; internal standard: TMS) δ: 2.33 (3H, s), 4.63 (1H, s), 5.31 (2H, s), 7.14–7.84 (13H, m)

(e) A suspension of 15 mg Compound(d)-A and 10 mg R(−)-mandelic acid in 1.5 ml water-containing benzene was heated until the compounds were dissolved, and this solution was allowed to cool. The crystals which separated out were collected by filtration, thus giving 15 mg of (+)-3-amino- 1,3-dihydro-1-(4'-methylphenacyl)-5-phenyl-2H-1,4-benzodiazepin- 2-one-2[R(−)-mandelate]•monohydrate (diastereomer A; starting material in Example 18).

Separately, 9 mg Compound(d)-B and 8 mg S(+)-mandelic acid were allowed to react in much the same manner as above, thus giving 8 mg of (−)-3-amino-1,3-dihydro-1-(4'-methylphenacyl)- 5-phenyl-2H-1,4-benzodiazepin-2-one•2[S(+)-mandelate]•monohydrate (diastereomer B; starting material in Example 19).

PHYSICOCHEMICAL PROPERTIES

Diastereomer A
Specific rotation $[\alpha]_D$=+47.96 (c=1.03, MeOH)

| Elemental analysis (as $C_{24}H_{21}N_3O_2 \cdot 2C_8H_8O_3 \cdot H_2O$) | | | |
|---|---|---|---|
| | C (%) | H (%) | N (%) |
| Calcd. | 68.07 | 5.57 | 5.95 |
| Found | 68.23 | 5.33 | 5.96 |

Diastereomer B
Specific rotation $[\alpha]_D$=−50.68 (c=1.10, MeOH)
NMR spectrum (DMSO; internal standard: TMS) δ: 2.34 (3H, s), 4.89 (1H, s), 5.08 (2H, s), 5.25–5.40 (2H, m), 7.10–7.85 (18H, m)

REFERENCE EXAMPLE 17

Starting materials in Examples 18 and 19

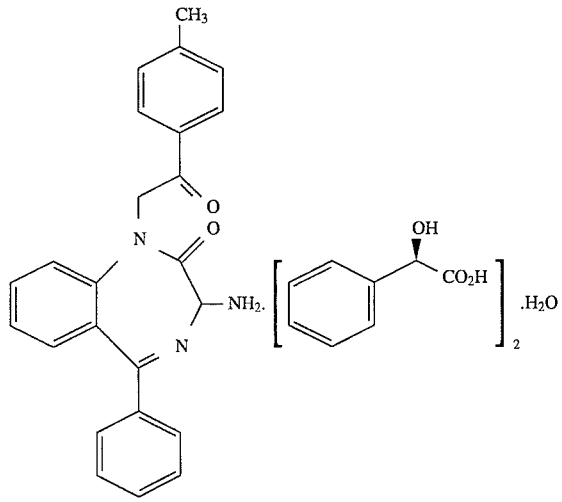

Diastereomer A

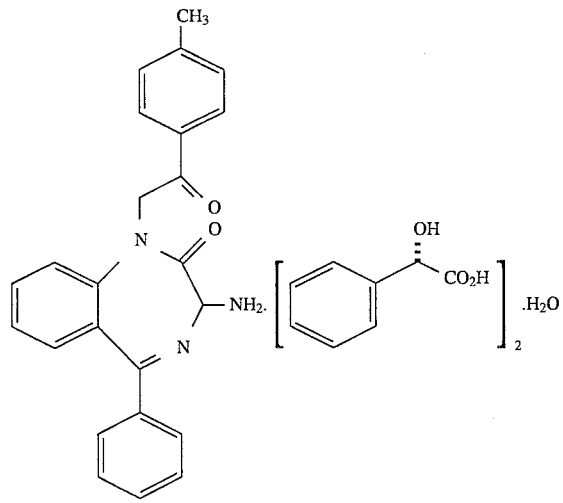

Diastereomer B

A suspension of 2.16 g 3-amino-1,3-dihydro-1-(4'-methylphenacyl)- 5-phenyl-2H-1,4-benzodiazepin-2-one, 1.71 g R(−)-mandelic acid and 32 mg 3,5-dichlorosalicylaldehyde in ml water-containing benzene was heated until the compounds were dissolved, and this clear solution was allowed to cool to room temperature.

A small amount of diastereomer A obtained in Paragraph (c) of Reference Example 16 was then added, the mixture was stirred at room temperature for three days, and the crystals which separated out were collected by filtration, thus giving 3.00 g of (+)-3-amino-1,3-dihydro-1-( 4'-methylphenacyl)-5-phenyl-2H-1,4-benzodiazepin-2-one•2[R(−)-mandelate]•monohydrate. The specific rotation and NMR spectrum of this compound were completely the same as those of diastereomer A of Reference Example 16.

(−)-3-Amino-1,3-dihydro-1-(4-methylphenacyl)-5-phenyl- 2H-1,4-benzodiazepin-2-one•2[S(+)-mandelate]•monohydrate (226 mg) was obtained from 200 mg diastereomer B, 159 mg S(+)-mandelic acid and 3 mg 3,5-dichlorosalicylaldehyde in the same manner as above. The physicochemical properties of this compound were completely the same as those of diastereomer-B.

REFERENCE EXAMPLE 18

Starting materials in Example 16 and Examples 20–25

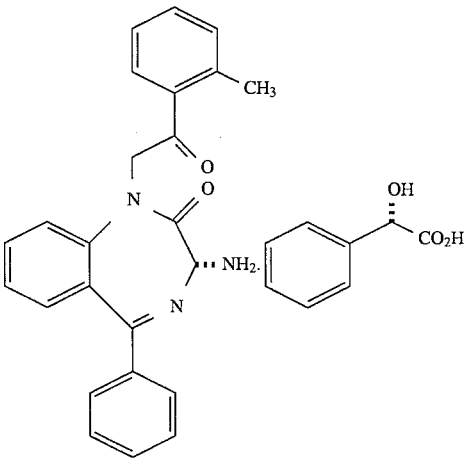

To a solution of 2.75 g 3-amino-1,3-dihydro-1-(2'-methylphenacyl)- 5-phenyl-2H-1,4-benzodiazepin-2-one in 55 ml acetonitrile, was added 0.98 g (S)(+)-mandelic acid, the mixture was stirred at room temperature for 30 minutes, 41 mg 3,5-dichlorosalicylaldehyde was then added, and stirring was further continued for 18 hours. The crystals which separated out were collected by filtration and washed with 15 ml acetonitrile, thus giving 2.94 g of (R)-3-amino-1,3-dihydro- 1-(2'-methylphenacyl)-5-phenyl-2H-1,4-benzodiazepin-2-one•(S)-mandelate.

PHYSICOCHEMICAL PROPERTIES $[\alpha]_D^{20}$=+152.5° (c=1.00, MeOH)
Melting point: 157°–160° C.

| Elemental analysis (as $C_{24}H_{21}N_3O_2 \cdot C_8H_8O_3$) | | | |
|---|---|---|---|
| | C (%) | H (%) | N (%) |
| Calcd. | 71.76 | 5.46 | 7.85 |
| Found | 71.64 | 5.49 | 7.79 |

The compound of Reference Example 19 was obtained in the same manner as in Reference Example 18.

REFERENCE EXAMPLE 19

Starting material in Example 17

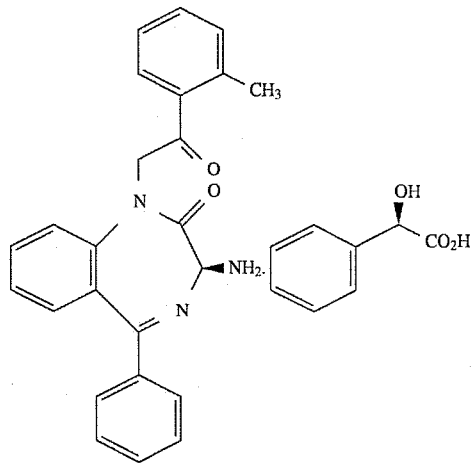

Name of the product
  (S)-3-Amino-1,3-dihydro-1-(2'-methylphenacyl)-5-phenyl- 2H-1,4-benzodiazepin-2-one•(R)mandelate
Starting materials:
  3-Amino-1,3-dihydro-1-(2'-methylphenacyl)-5-phenyl- 2H-1,4-benzodiazepin-2-one, (R)(−)-mandelic acid, and 3,5-dichlorosalicylaldehyde

PHYSICOCHEMICAL PROPERTIES $[\alpha]_D^{20}$=151.2° (c=1.00, MeOH)
Melting point: 157°–160° C.

| Elemental analysis (as $C_{14}H_{21}N_3O_2 \cdot C_8H_8O_3$) | | | |
|---|---|---|---|
| | C (%) | H (%) | N (%) |
| Calcd. | 71.76 | 5.46 | 7.85 |
| Found | 71.74 | 5.56 | 7.86 |

The compound of Reference Example 20 was obtained in the same manner as in Reference Example 1 or 2.

REFERENCE EXAMPLE 20

Starting material in Example 26

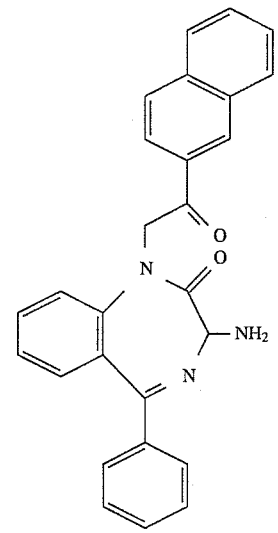

Name of the objective product
  3-Amino-1,3-dihydro-1-(2'-naphthoylmethyl)-5-phenyl- 2H-1,4-benzodiazepin-2-one
Starting materials:
  1,3-Dihydro-1-(2'-naphthoylmethyl)-3-oxyimido-5-phenyl- 2H-1,4-benzodiazepin-2-one

PHYSICOCHEMICAL PROPERTIES

Mass spectrometric analysis, FAB, Pos(m/z): 420 ($M^+$+1)
NMR spectrum (CDCl$_3$; internal standard: TMS) δ: 2.78 (2H, br), 4.71 (1H, s), 5.37 (1H, d), 5.59 (1H, d), 7.0–8.1 (15H, m), 8.42 (1H, s)

EXAMPLE 1

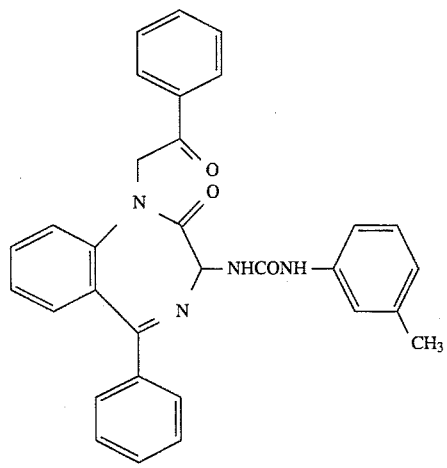

To a mixture of 0.74 g 3-amino-1,3-dihydro-1-phenacyl-5-phenyl-2H-1,4-benzodiazepin-2-one and 5 ml tetrahydrofuran, was added a solution of 0.27 g 3-tolyl isocyanate in 3 ml tetrahydrofuran, and the resulting mixture was stirred at room temperature for four hours. The solvent was distilled off from the reaction mixture, and the residue was recrystallized from a mixture of toluene and n-hexane, thus giving 0.78 g of 1-[2,3-dihydro-2-oxo-1-phenacyl-5-phenyl-1H-1,4-benzodiazepin-3-yl]-3-(3-tolyl)urea.

PHYSICOCHEMICAL PROPERTIES

Melting point: 212°–214° C.

| | Elemental analysis (as $C_{31}H_{26}N_4O_3$) | | |
|---|---|---|---|
| | H (%) | H (%) | N (%) |
| Calcd. | 74.09 | 5.21 | 11.15 |
| Found | 74.21 | 5.26 | 11.08 |

Mass spectrometric analysis, FAB, Pos(m/z): 503 ($M^+$+1)

EXAMPLE 2

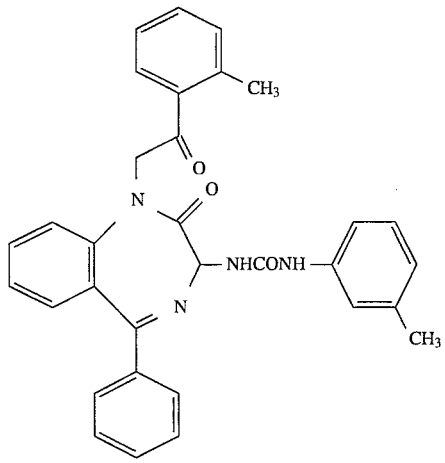

To a mixture of 5.75 g 3-amino-1,3-dihydro-1-(2'-methylphenacyl)-5-phenyl-2H-1,4-benzodiazepin-2-one and 60 ml tetrahydrofuran, was added a solution of 2.24 g 3-tolyl isocyanate in 5 ml tetrahydrofuran, and the resulting mixture was stirred at room temperature for 1.5 hours. The solvent was distilled off from the reaction mixture, and the residue was recrystallized from a mixture of dichloromethane and diethyl ether, thus giving 7.01 g of 1-[2,3-dihydro-1-(2'-methylphenacyl)-2-oxo-5-phenyl-1H-1,4-benzodiazepin-3-yl]-3-(3-tolyl)urea.

PHYSICOCHEMICAL PROPERTIES

Melting point: 141°–143° C.

| | Elemental analysis (as $C_{32}H_{28}N_4O_3$) | | |
|---|---|---|---|
| | C (%) | H (%) | N (%) |
| Calcd. | 74.40 | 5.46 | 10.85 |
| Found | 74.43 | 5.49 | 10.83 |

Mass spectrometric analysis, FAB, Pos(m/z): 517 ($M^+$+1)

The compound of the following Examples were prepared in the same way as in Example 1 or 2.

EXAMPLE 3

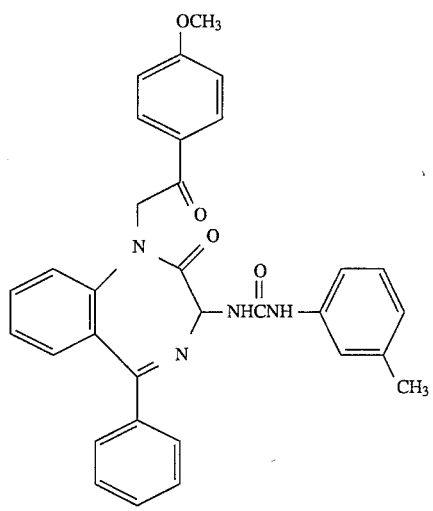

Name of the product
1-[2,3-Dihydro-1-(4'-methoxyphenacyl)-2-oxo-5-phenyl-1H-1,4-benzodiazepin-3-yl]-3-(3-tolyl)urea
Starting materials:
3-Amino-1,3-dihydro-1-(4'-methoxyphenacyl)-5-phenyl-2H-1,4-benzodiazepin-2-one, and 3-tolyl isocyanate

PHYSICOCHEMICAL PROPERTIES

Melting point: 175°–178° C.

| | Elemental analysis (as $C_{32}H_{28}N_4O_4$) | | |
|---|---|---|---|
| | C (%) | H (%) | N (%) |
| Calcd. | 72.17 | 5.30 | 10.52 |
| Found | 72.20 | 5.60 | 10.23 |

Mass spectrometric analysis, FAB, Pos (m/z): 533 ($M^+$+1)

EXAMPLE 4

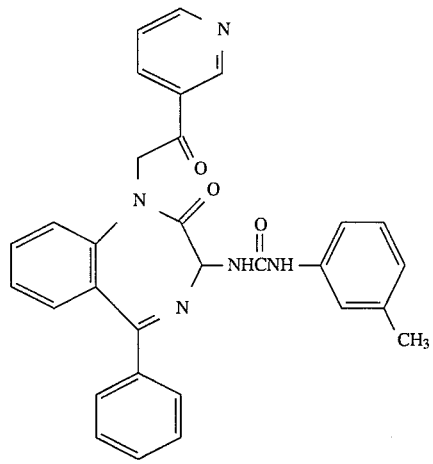

Name of the product

1-[2,3-Dihydro-1-nicotinoylmethyl-2-oxo-5-phenyl-1H-1,4-benzodiazepin-3-yl]-3-(3-tolyl)urea Starting materials:

3-Amino-1,3-dihydro-1-nicotinoylmethyl-5-phenyl-2H-1,4-benzodiazepin-2-one, and 3-tolyl isocyanate

PHYSICOCHEMICAL PROPERTIES

Melting point: 239°–241° C.

| Elemental analysis (as $C_{30}H_{25}N_5O_3$) | | | |
|---|---|---|---|
| | C (%) | H (%) | N (%) |
| Calcd. | 71.56 | 5.00 | 13.91 |
| Found | 71.57 | 5.20 | 13.80 |

Mass spectrometric analysis, ST (m/z): 503 ($M^+$)

EXAMPLE 5

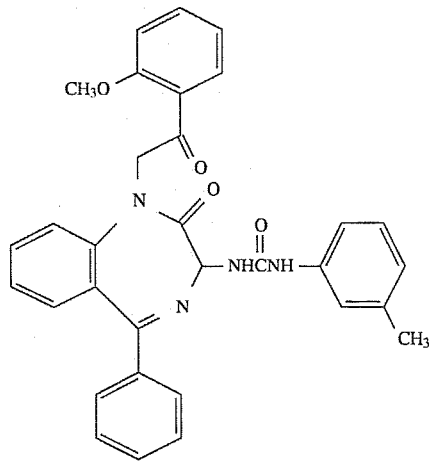

Name of the product

1-[2,3-Dihydro-1-(2'-methoxyphenacyl)-2-oxo-5-phenyl-1H-1,4-benzodiazepin-3-yl]-3-(3-tolyl)urea Starting materials:

3-Amino-1,3-dihydro-1-(2'-methoxyphenacyl)-5-phenyl-2H-1,4-benzodiazepin-3-one, and 3-tolyl isocyanate

PHYSICOCHEMICAL PROPERTIES

Melting point: 160°–163° C.

| Elemental analysis (as $C_{32}H_{28}N_4O_4 \cdot 0.5H_2O$) | | | |
|---|---|---|---|
| | C (%) | H (%) | N (%) |
| Calcd. | 70.95 | 5.41 | 10.35 |
| Found | 70.74 | 5.28 | 10.23 |

Mass spectrometric analysis, FAB, Pos (m/z): 533 ($M^+$+1)

EXAMPLE 6

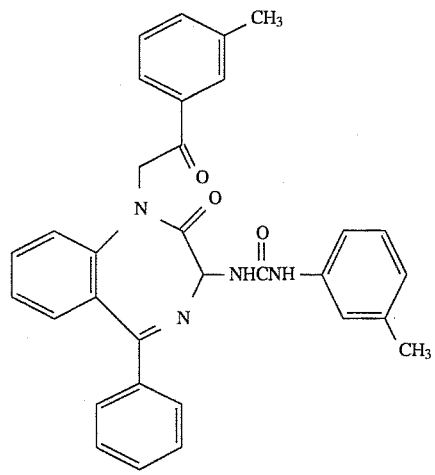

Name of the product

1-[2,3-Dihydro-1-(3'-methylphenacyl)-2-oxo-5-phenyl-1H-1,4-benzodiazepin-3-yl]-3-(3-tolyl)urea Starting materials:

3-Amino-1,3-dihydro-1-(3'-methylphenacyl)-5-phenyl-2H-1,4-benzodiazepin-2-one, and 3-tolyl isocyanate

PHYSICOCHEMICAL PROPERTIES

Melting point: 225°–227° C.

| Elemental analysis (as $C_{32}H_{28}N_4O_3$) | | | |
|---|---|---|---|
| | C (%) | H (%) | N (%) |
| Calcd. | 74.40 | 5.46 | 10.85 |
| found | 74.38 | 5.43 | 10.72 |

Mass spectrometric analysis, FAB, Pos(m/z): 517 ($M^+$+1)

EXAMPLE 7

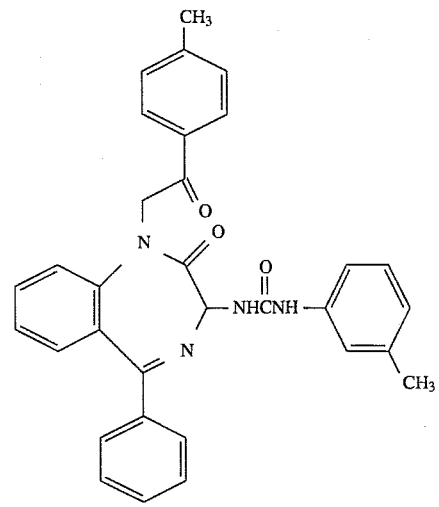

Name of the product

1-[2,3-Dihydro-1-(4'-methylphenacyl)-2-oxo-5-phenyl-1H-1,4-benzodiazepin-3-yl]-3-(3-tolyl)urea Starting materials:

3-Amino-1,3-dihydro-1-(4'-methylphenacyl)-5-phenyl-
2H-1,4-benzodiazepin-2-one, and 3-tolyl isocyanate

PHYSICOCHEMICAL PROPERTIES

Melting point: 193°–196° C.

| Elemental analysis (as $C_{32}H_{28}N_4O_3$) | | | |
|---|---|---|---|
| | C (%) | H (%) | N (%) |
| Calcd. | 74.40 | 5.46 | 10.85 |
| Found | 74.56 | 5.50 | 10.77 |

Mass spectrometric analysis, FAB, Pos(m/z): 517 ($M^+$+1)

EXAMPLE 8

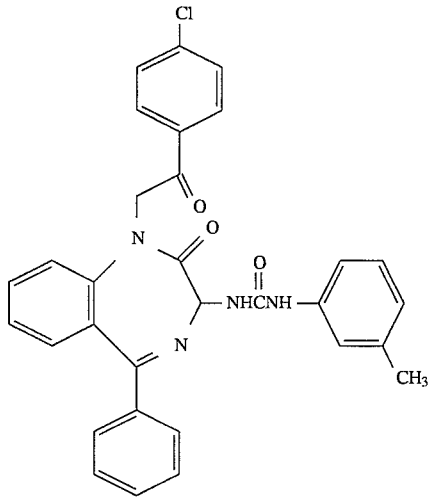

Name of the product

1-[1-(4'-Chlorophenacyl)-2,3-dihydro-2-oxo-5-phenyl-
1H-1,4-benzodiazepin-3-yl]-3-(3-tolyl)urea Starting materials:

3-Amino-1-(4'-chlorophenacyl)-1,3-dihydro-5-phenyl-
2H-1,4-benzodiazepin-2-one, and 3-tolyl isocyanate

PHYSICOCHEMICAL PROPERTIES

Melting point: 214°–216° C.

| Elemental analysis (as $C_{31}H_{25}NH_4O_3Cl$) | | | | |
|---|---|---|---|---|
| | C (%) | H (%) | N (%) | Cl (%) |
| Calcd. | 69.34 | 4.69 | 10.43 | 6.60 |
| Found | 69.14 | 4.69 | 10.38 | 6.76 |

Mass spectrometric analysis, EI(m/z): 536 ($M^+$–1)

EXAMPLE 9

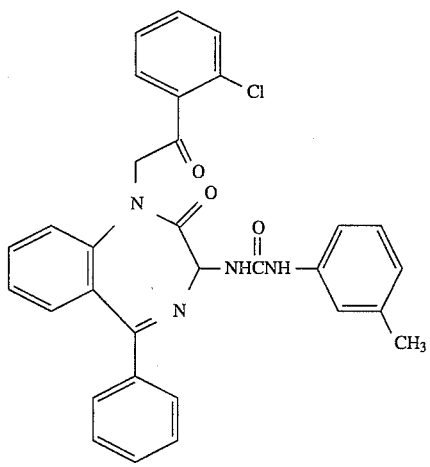

Name of the product

1-[1-(2'-Chlorophenacyl)-2,3-dihydro-2-oxo-5-phenyl-
1H-1,4-benzodiazepin-3-yl]-3-(3-tolyl)urea Starting materials:

3-Amino-1-(2'-chlorophenacyl)-1,3-dihydro-5-phenyl-
2H-1,4-benzodiazepin-2-one, and 3-tolyl isocyanate

PHYSICOCHEMICAL PROPERTIES

Melting point: 191°–193° C.

| Elemental analysis (as $C_{31}H_{25}N_4O_3Cl.0.3H_2O$) | | | | |
|---|---|---|---|---|
| | C (%) | H (%) | N (%) | Cl (%) |
| Calcd. | 68.63 | 4.77 | 10.33 | 6.54 |
| Found | 68.87 | 4.76 | 10.13 | 6.48 |

Mass spectrometric analysis, FAB, Pos (m/z): 537 ($M^+$)

EXAMPLE 10

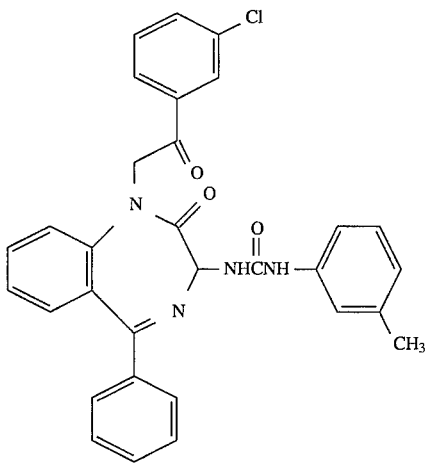

Name of the product

1-[1-(3'-Chlorophenacyl)-2,3-dihydro-2-oxo-5-phenyl-
1H-1,4-benzodiazepin-3-yl]-3-(3-tolyl)urea Starting materials:

3-Amino-1-(3'-chlorophenacyl)-1,3-dihydro-5-phenyl-
2H-1,4-benzodiazepin-2-one, and 3-tolyl isocyanate

37

PHYSICOCHEMICAL PROPERTIES

Melting point: 139°–142° C. (PhCH$_3$-C$_2$H$_5$OH)

| Elemental analysis (as C$_{31}$H$_{25}$N$_4$O$_3$Cl) | | | | |
|---|---|---|---|---|
| | C (%) | H (%) | N (%) | Cl (%) |
| Calcd. | 69.34 | 4.69 | 10.43 | 6.60 |
| Found | 69.24 | 4.70 | 10.39 | 6.58 |

Mass spectrometric analysis, EI (m/z): 536 (M$^+$–1)

EXAMPLE 11

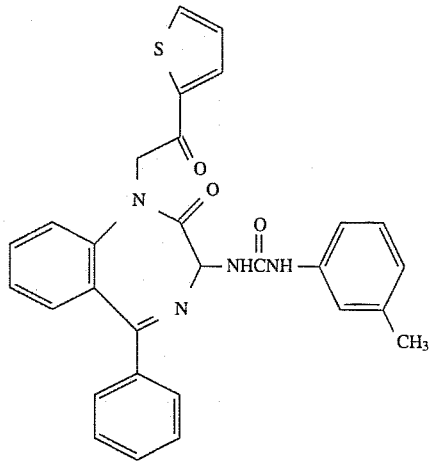

A mixture of 0.26 g 3-amino-1,3-dihydro-5-phenyl-1-(2-thenoyl)methyl-2H-1,4-benzodiazepin-2-one, 95 mg 3-tolylisocyanate and 5 ml tetrahydrofuran was stirred at room temperature for two hours. The solvent was distilled off from the reaction mixture under reduced pressure, a 1:1 mixture of toluene and diethyl ether (5 ml) was added to the residue, and the crystals were collected by filtration, thus giving 0.2 g of 1-[2,3-dihydro-2-oxo-5-phenyl-1-(2-thenoyl)methyl- 1H-1,4-benzodiazepin-3-yl]-3-(3-tolyl)urea.

This compound has the following physicochemical properties.

i) Melting point: 189°–192° C.

| ii) Elemental analysis (as C$_{29}$H$_{24}$N$_4$O$_3$) | |
|---|---|
| | S (%) |
| Calcd. | 6.30 |
| Found | 6.25 | iii) Mass spectrometric analysis, FAB, Pos(m/z): 509 (M$^+$+1)

The following compound was prepared in the same way as in Example 11.

38

EXAMPLE 12

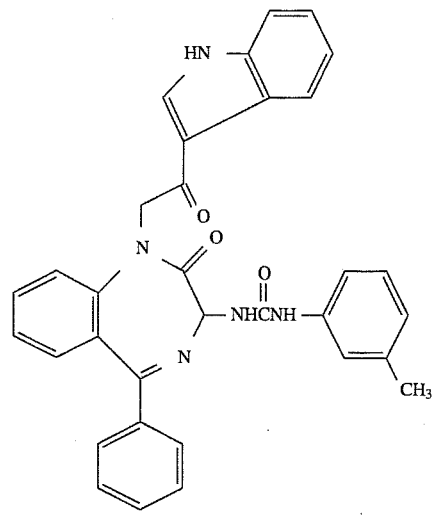

1-[2,3-Dihydro-1-(3-indolylcarbonyl)methyl-2-oxo-5-phenyl- 1H-1,4-benzodiazepin-3-yl]-3-(3-tolyl)urea Starting materials:

3-Amino-1,3-dihydro-1-(3-indolylcarbonyl)methyl-5-phenyl- 2H-1,4-benzodiazepin-2-one, and 3-tolyl isocyanate This compound has the following physicochemical properties.

i) Melting point: 232°–237° C.

| ii) Elemental analysis (as C$_{33}$H$_{27}$N$_5$O$_3$.0.1H$_2$O) | | | |
|---|---|---|---|
| | C (%) | H (%) | N (%) |
| Calcd. | 72.91 | 5.38 | 12.88 |
| Found | 72.76 | 5.17 | 12.71 | iii) Mass spectrometric analysis, FAB, Pos (m/z): 542 (M$^+$+1)

EXAMPLE 13

The following compound was obtained in the same way as in Example 11.

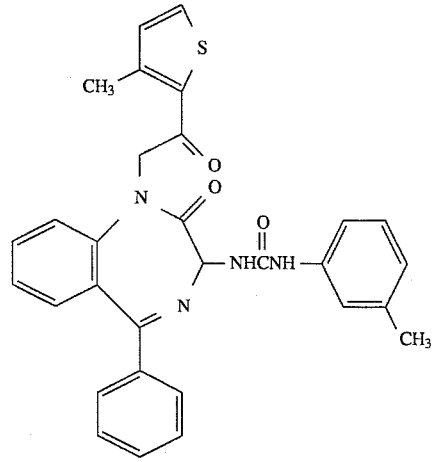

1-[2,3-Dihydro-1-(3-methyl-2-thenoyl)methyl-2-oxo-5-phenyl-1H-1,4-benzodiazepin-3-yl]-3-(3-tolyl)urea Starting materials:
3-Amino-1,3-dihydro-1-(3-methyl-2-thenoyl)methyl-5-phenyl-2H-1,4-benzodiazepin-2-one, and 3-tolyl isocyanate

PHYSICOCHEMICAL PROPERTIES i) Melting point: 150°–153° C.
ii) Mass spectrometric analysis, FAB, Pos(m/z): 523 ($M^+ +1$)
iii) NMR spectrum (DMSO-$d_6$; internal standard: TMS) δ: 2.25 (3H, s), 2.53 (3H, s), 5.32 (2H, s), 5.42 (1H, d), 6.78 (1H, d), 7.0–7.8 (14H, m), 7.94 (1H, d), 9.01 (1H, s)

EXAMPLE 14

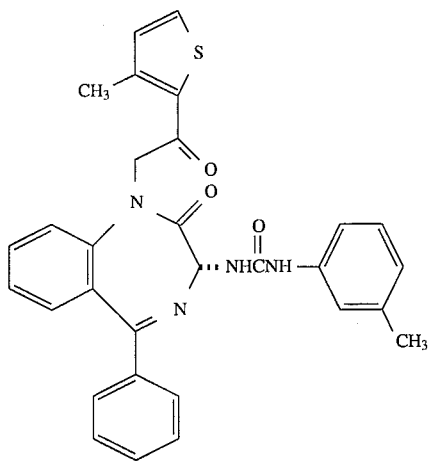

A mixture of 5.1 g (R)-3-amino-1,3-dihydro-1-(3-methyl-2-thenoyl)methyl-5-phenyl-2H-1,4-benzodiazepin-2-one•(S)-mandelate, 18 ml 1N aqueous solution of caustic soda, 50 ml water and 20 ml dichloromethane was stirred under ice cooling for 30 minutes. The reaction mixture was extracted with dichloromethane, the extract was dried over anhydrous sodium sulfate, and the solvent was distilled off under reduced pressure, giving 3.7 g of free amine.

A mixture of this free amine, 1.26 g 3-tolyl isocyanate and 27 ml tetrahydrofuran was stirred at room temperature for five hours, the solvent was distilled off from the reaction mixture under reduced pressure, 50 ml acetonitrile was added to the residue, and the crystals which separated out were collected by filtration, thus giving 4.5 g of (R)-1-[2,3-dihydro-1-(3-methyl-2-thenoyl)methyl-2-oxo-5-phenyl-1H-1,4-benzodiazepin-3-yl]-3-(3-tolyl)urea as white crystals.

PHYSICOCHEMICAL PROPERTIES i) $[\alpha]_D^{20} = -158°$ (c=1.0, $CH_2Cl_2$)
ii) Melting point: 203°–206° C.

| iii) Elemental analysis (as $C_{30}H_{26}N_4O_3S$) | | | | |
| --- | --- | --- | --- | --- |
|  | C (%) | H (%) | N (%) | S (%) |
| Calcd. | 68.95 | 5.01 | 10.72 | 6.14 |
| Found | 69.11 | 5.19 | 10.71 | 6.04 |

EXAMPLE 15

The following compound was prepared in the same way as in Example 14.

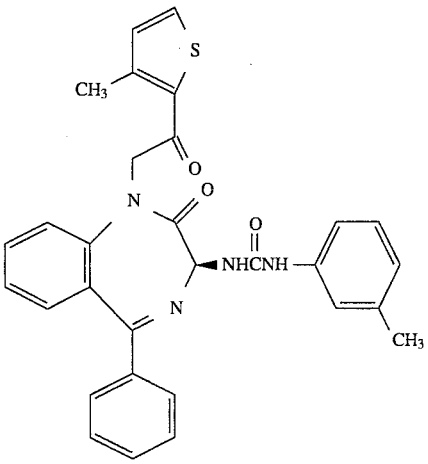

(S)-1-[2,3-Dihydro-1-(3-methyl-2-thenoyl)methyl-2-oxo-5-phenyl-1H-1,4-benzodiazepin-3-yl]-3-(3-tolyl)urea Starting materials:
(S)-3-Amino-1,3-dihydro-1-(3-methyl-2-thenoyl)methyl-5-phenyl-2H-1,4-benzodiazepin-2-one•(R)-mandelate, and 3-tolyl isocyanate

PHYSICOCHEMICAL PROPERTIES i) $[\alpha]_D^{20} = -158°$ (c=10, $CH_2Cl_2$)
ii) Melting point: 204°–206° C.
iii) Elemental analysis (as $C_{30}H_{26}N_4O_3S$)

|  | C (%) | H (%) | N (%) | S (%) |
| --- | --- | --- | --- | --- |
| Calcd. | 68.95 | 5.01 | 10.72 | 6.14 |
| Found | 69.01 | 5.03 | 10.66 | 6.07 |

EXAMPLE 16

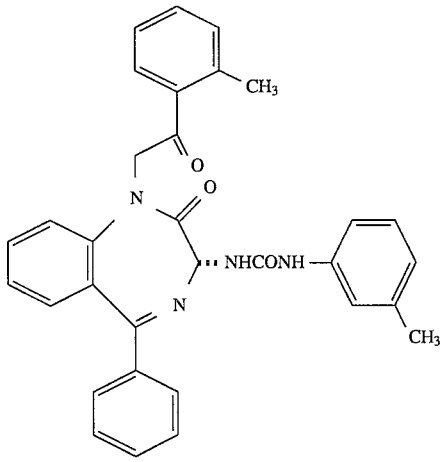

To a solution of 2.87 g (R)-3-amino-1,3-dihydro-1-(2'-methylphenacyl)-5-phenyl-2H-1,4-benzodiazepin-2-one•(S)-mandelate in 60 ml dichloromethane, was added 40 ml 0.25N aqueous solution of caustic soda, and the mixture was stirred for ten minutes. The organic layer collected was washed with water and saturated aqueous solution of sodium chloride in that order, and the dried over anhydrous magnesium sulfate. The solvent was distilled off from the dried solution, and the free amine thus obtained was allowed to react with 0.75 g 3-tolyl isocyanate in the same way as in Example 1 or 2, thus giving 2.39 g of (R)-1-[2,3-dihydro-1-(2'-methylphenacyl)-2-oxo- 5-phenyl-1H-1,4-benzodiazepin-3-yl]-3-(3-tolyl)urea.

PHYSICOCHEMICAL PROPERTIES $[\alpha]\alpha_D^{20} = +138.1°$ (c=0.99, $CH_2Cl_2$)

Melting point: 197°–199° C.

| | Elemental analysis (as $C_{32}H_{28}N_4O_3$) | | |
|---|---|---|---|
| | C (%) | H (%) | N (%) |
| Calcd. | 74.40 | 5.46 | 10.85 |
| Found | 74.45 | 5.53 | 10.88 |

Mass spectrometric analysis, FAB, Pos(m/z): 517 ($M^+$+1)

The compounds of Examples 17 through 25 were prepared in the same way as in Example 16.

EXAMPLE 17

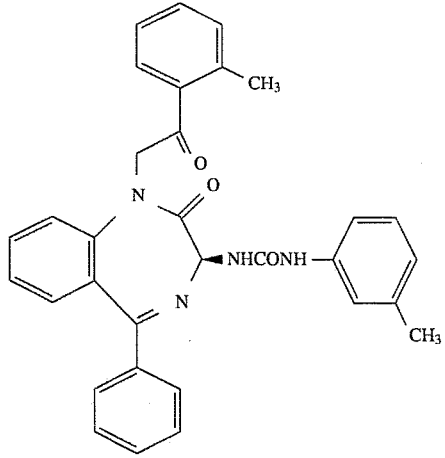

(S)-1-[2,3-Dihydro-1-(2'-methylphenacyl)-2-oxo-5-phenyl- 1H-1,4-benzodiazepin-3-yl]-3-(3-tolyl)urea Starting materials:

(S)-3-Amino-1,3-dihydro-1-(2'-methylphenacyl)-5-phenyl- 2H-1,4-benzodiazepin-2-one•(R)-mandelate, and 3-tolyl isocyanate

PHYSICOCHEMICAL PROPERTIES $[\alpha]_D^{20} = -136.9°$ (c=1.01, $CH_2Cl_2$)

Melting point: 194°–198° C.

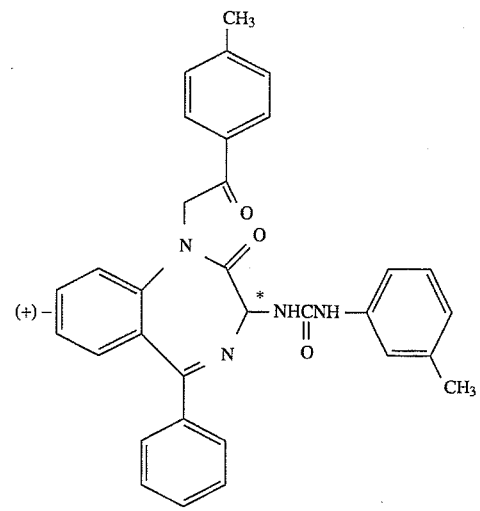

Mass spectrometric analysis, FAB, Pos(m/z): 517 ($M^+$+1)

Example 18

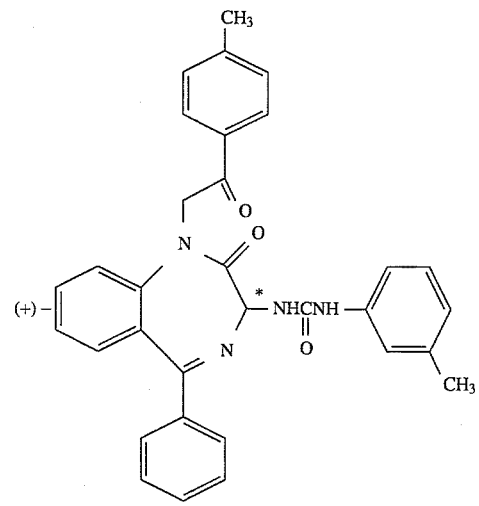

(+)-1-[2,3-Dihydro-1-(4'-methylphenacyl)-5-phenyl-1H-1,4-benzodiazepin-2-on-3-yl]-3-(3-methylphenyl)urea Starting materials:

(+)-3-Amino-1,3-dihydro-1-(4'-methylphenacyl)-5-phenyl- 2H-1,4-benzodiazepin-2-one•2[R(−)-mandelate] •monohydrate, and 3-tolyl isocyanate

PHYSICOCHEMICAL PROPERTIES $[\alpha]_D^{20} = +88.3°$ (c=1.00, MeOH)

Melting point: 130°–138° C.

| | Elemental analysis (as $C_{32}H_{28}N_4O_3$) | | |
|---|---|---|---|
| | C (%) | H (%) | N (%) |
| Calcd. | 74.40 | 5.46 | 10.85 |
| Found | 74.52 | 5.61 | 10.70 |

Mass spectrometric analysis, FAB, Pos(m/z): 517 ($M^+$+1)

EXAMPLE 19

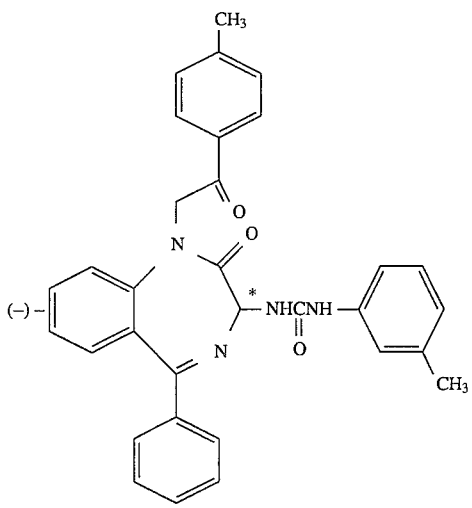

(−)-1-[2,3-Dihydro-1-(4'-methylphenacyl)-5-phenyl-1H-1,4-benzodiazepin-2-on-3-yl]-3-(3-methylphenyl)urea Starting materials:
(−)-3-Amino-1,3-dihydro-1-(4'-methylphenacyl)-5-phenyl- 2H-1,4-benzodiazepin-2-one•2[S(+)-mandelate]•monohydrate, and 3-tolyl isocyanate

PHYSICOCHEMICAL PROPERTIES $[\alpha]_D^{20} = -86.3°$ (c=1.02, MeOH)
Melting point: 143°–145° C.

| Elemental analysis (as $C_{32}H_{28}N_4O_3$) | | | |
|---|---|---|---|
| | C (%) | H (%) | N (%) |
| Calcd. | 74.40 | 5.46 | 10.85 |
| Found | 74.11 | 5.58 | 10.69 |

Mass spectrometric analysis, FAB, Pos(m/z): 517 (M$^+$+1)

EXAMPLE 20

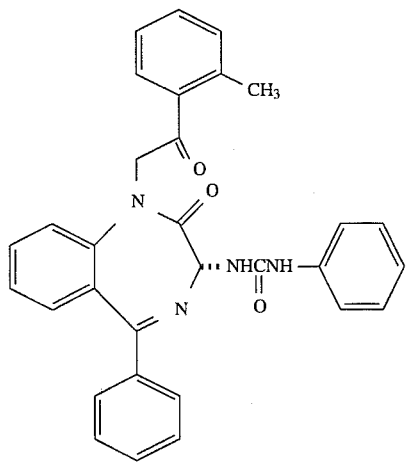

(R)-1-[2,3-Dihydro-1-(2'-methylphenacyl)-5-phenyl-1H-1,4-benzodiazepin-2-on-3-yl]-3-phenylurea Starting materials:
(R)-3-Amino-2,3-dihydro-1-(2'-methylphenacyl)-5-phenyl- 2H-1,4-benzodiazepin-2-one•S(+)-mandelate, and 3-tolyl isocyanate

PHYSICOCHEMICAL PROPERTIES $[\alpha]_D^{20} = +128.7°$ (c=1.00, CHCl$_3$)
Melting point: 229°–231° C.

| Elemental analysis (as $C_{31}H_{26}N_4O_3$) | | | |
|---|---|---|---|
| | C (%) | H (%) | N (%) |
| Calcd. | 74.09 | 5.21 | 11.15 |
| Found | 74.07 | 5.33 | 11.00 |

Mass spectrometric analysis, FAB, Pos(m/z): 503 (M$^+$+1)

EXAMPLE 21

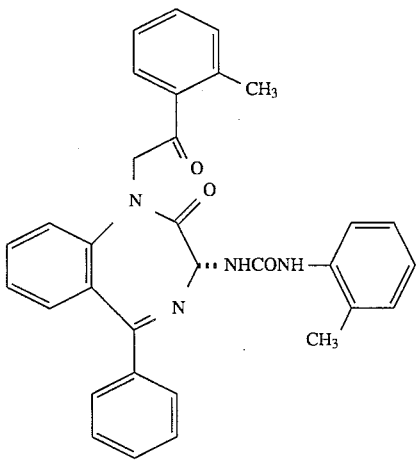

(R)-1-[2,3-Dihydro-1-(2'-methylphenacyl)-2-oxo-5-phenyl- 1H-1,4-benzodiazepin-3-yl]-3-(2-tolyl)urea Starting materials:
(R)-3-Amino-1,3-dihydro-1-(2'-methylphenacyl)-5-phenyl- 2H-1,4-benzodiazepin-2-one•(S)-mandelate, and 2-tolyl isocyanate

PHYSICOCHEMICAL PROPERTIES $[\alpha]_D^{20} = +151.8°$ (c=1.03, CH$_2$Cl$_2$)
Melting point: 178°–181° C.

| Elemental analysis (as $C_{32}H_{28}N_4O_3$) | | | |
|---|---|---|---|
| | C (%) | H (%) | N (%) |
| Calcd. | 74.40 | 5.46 | 10.85 |
| Found | 74.34 | 5.45 | 10.84 |

Mass spectrometric analysis, FAB, Pos(m/z): 517 (M$^+$+1)

EXAMPLE 22

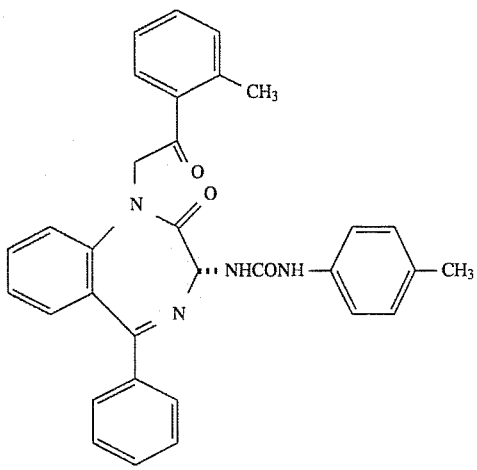

(R)-1-[2,3-Dihydro-1-(2'-methylphenacyl)-2-oxo-5-phenyl- 1H-1,4-benzodiazepin-3-yl]-3-(4-tolyl)urea
Starting materials:
(R)-3-Amino-1,3-dihydro-1-(2'-methylphenacyl)-5-phenyl- 2H-1,4-benzodiazepin-2-one•(S)-mandelate, and 4-tolyl isocyanate

PHYSICOCHEMICAL PROPERTIES $[\alpha]_D^{20}$=+149.6° (c=0.39, DMF)
Melting point: 256°–295° C.

| | Elemental analysis (as $C_{32}H_{28}N_4O_3$) | | |
|---|---|---|---|
| | C (%) | H (%) | N (%) |
| Calcd. | 74.40 | 5.46 | 10.85 |
| Found | 74.33 | 5.60 | 10.68 |

Mass spectrometric analysis, FAB, Pos(m/z): 517 ($M^+$+1)

EXAMPLE 23

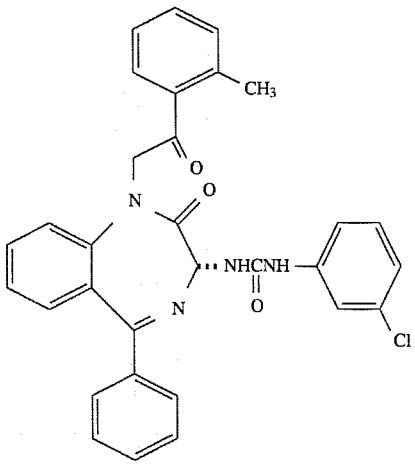

(R)-1-(3-Chlorophenyl)-3-[2,3-dihydro-1-(2'-methylphenacyl)- 5-phenyl -1H-1,4-benzodiazepin-2on-3-yl]urea
Starting materials:
(R)-3-Amino-2,3-dihydro-1-(2'-methylphenacyl)-5-phenyl- 2H-1,4-benzodiazepin-2-one•S(+)-mandelate, and 3-chlorophenyl isocyanate

PHYSICOCHEMICAL PROPERTIES $[\alpha]_D^{20}$=+115.8° (c=1.00, $CHCl_3$)
Melting point: 132°–133° C.

| | Elemental analysis (as $C_{31}H_{25}N_4O_3Cl.0.2H_2O$) | | | |
|---|---|---|---|---|
| | C (%) | H (%) | N (%) | Cl (%) |
| Calcd. | 68.87 | 4.74 | 10.36 | 6.56 |
| Found | 68.73 | 4.75 | 10.39 | 6.74 |

Mass spectrometric analysis, FAB, Pos(m/z): 537 ($M^+$+1)

EXAMPLE 24

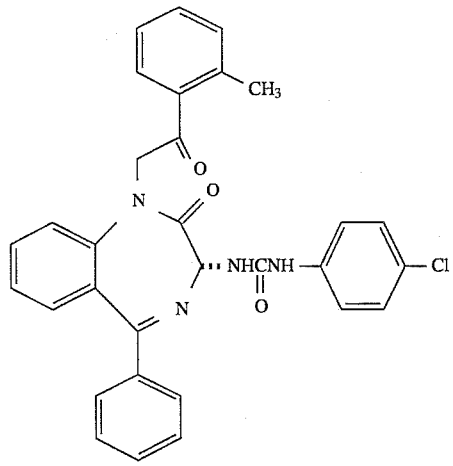

(R)-1-[4-Chlorophenyl)-3-[2,3-dihydro-1-(2'-methylphenacyl)- 5-phenyl-1H-1,4-benzodiazepin-2-on-3-yl]urea
Starting materials:
(R)-3-Amino-2,3-dihydro-1-(2'-methylphenacyl)-5-phenyl- 2H-1,4-benzodiazepin-2-one•S(+)-mandelate, and 4-chlorophenyl isocyanate

PHYSICOCHEMICAL PROPERTIES $[\alpha]_D$=+134.9° (c=1.00, DMF)
Melting point: 244°–246° C.

| | Elemental analysis (as $C_{31}H_{25}N_4O_3Cl$) | | | |
|---|---|---|---|---|
| | C (%) | H (%) | N (%) | Cl (%) |
| Calcd. | 69.34 | 4.69 | 10.43 | 6.60 |
| Found | 69.16 | 4.75 | 10.37 | 6.59 |

Mass spectrometric analysis, FAB, Pos(m/z): 537 ($M^+$+1)

EXAMPLE 25

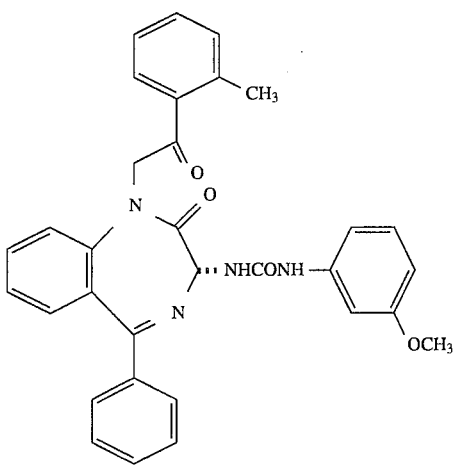

(R)-1-[2,3-dihydro-1-(2'-methylphenacyl)-2-oxo-5-phenyl- 1H-1,4-benzodiazepin-3-yl]-3-(3-methoxyphenyl)urea Starting materials:

(R)-3-Amino-1,3-dihydro-1-(2'-methylphenacyl)-2-oxo- 5-phenyl-2H-1,4-benzodiazepin-2-one•(S)-mandelate, and 3-methoxyphenyl isocyanate

PHYSICOCHEMICAL PROPERTIES $[\alpha]_D^{20} = +151.5°$ (c=0.31, $CH_2Cl_2$)

Melting point: 192°–195° C.

| | Elemental analysis (as $C_{32}H_{28}N_4O_4$) | | |
|---|---|---|---|
| | C (%) | H (%) | N (%) |
| Calcd. | 72.17 | 5.30 | 10.52 |
| Found | 72.11 | 5.32 | 10.51 |

Mass spectrometric analysis, FAB, Pos(m/z): 533 ($M^+$+1)

The compound of Example 26 was prepared in the same way as in Example 1 or 2.

EXAMPLE 26

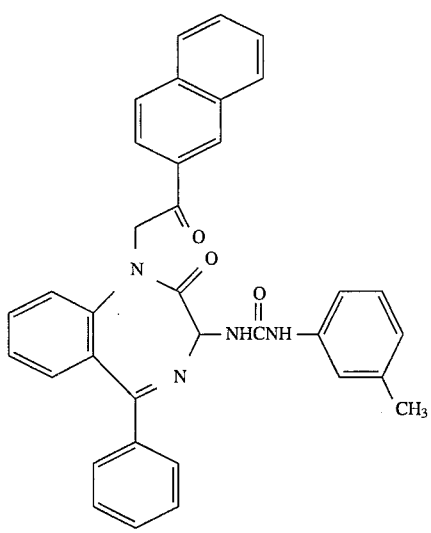

1-[2,3-Dihydro-1-(2-naphthoylmethyl)-2-oxo-5-phenyl- 1H-1,4-benzodiazepin-3-yl]-3-(3-tolyl)urea Starting materials:

3-Amino-1,3-dihydro-1-(2-naphthoylmethyl)-5-phenyl- 2H-1,4-benzodiazepin-2-one, and 3-tolyl isocyanate

PHYSICOCHEMICAL PROPERTIES

Melting point: 204°–206° C. ($PhCH_3$-$Et_2O$)

| | Elemental analysis (as $C_{35}H_{28}N_4O_3$) | | |
|---|---|---|---|
| | C (%) | H (%) | N (%) |
| Calcd. | 76.07 | 5.11 | 10.14 |
| Found | 75.96 | 5.14 | 10.08 |

Mass spectrometric analysis, FAB, Pos (m/z): 553 (M+1)

NMR spectrum (DMSO-$d_6$; internal standard: TMS) δ: 2.25 (3H, s), 5.42 (1H, d), 5.69 (1H, d), 5.78 (1H, d), 6.76 (1H, d), 7.0–7.8 (15H, m), 7.9–8.2 (4H, m), 8.80 (1H, s), 9.00 (1H, s)

We claim:

1. A novel benzodiazepine derivative represented by the following formula or a pharmaceutically acceptable salt thereof,

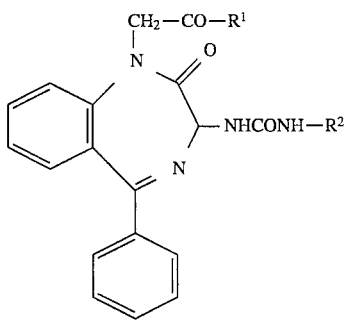

wherein $R^1$ is an aryl group, or an aromatic heterocyclic radical of 5-membered monocyclic, 6-membered monocyclic or 5- and 6-membered bicyclic structure, which may optionally be substituted; and $R^2$ is an aryl group which may optionally be substituted.

2. The novel benzodiazepine derivative or a pharmaceutically acceptable salt thereof as defined in claim 1, wherein $R^1$ is an aryl group which may optionally be substituted with a lower alkyl group, a lower alkoxy group or a halogen atom.

3. The novel benzodiazepine derivative or a pharmaceutically acceptable salt thereof as defined in claim 1, wherein $R^1$ is a 5-membered heterocyclic radical which may optionally be substituted with a lower alkyl group, a lower alkoxy group or a halogen atom.

4. The benzodiazepine derivative of claim 1 which is 1-[2-3-Dihydro-1-(2'-methylphenacyl)-2-oxo-5-phenyl-1H-1,4-benzodiazepine- 3-yl]-3-(3-tolyl)urea or a pharmaceutically acceptable salt thereof.

5. The benzodiazepine derivative of claim 1 which is (R)-1-[2,3-Dihydro-1-(2'-methylphenacyl)-2-oxo-5-phenyl-1H-1,4 -benzodiazepin-3-yl]-3-(3-tolyl)urea or a pharmaceutically acceptable salt thereof.

6. The benzodiazepine derivative of claim 1 which is 1-[2,3-Dihydro-1-(3-methyl-2-thenoyl)methyl-2-oxo-5- phenyl-1H-1,4-benzodiazepin-3-yl]-3-(3-tolyl)urea or a pharmaceutically acceptable salt thereof.

7. The benzodiazepine derivative of claim 1 which is (R)-1-[2,3-Dihydro-1-(3-methyl-2-thenoyl)methyl-2-oxo-5-phenyl-1H-1,4-benzodiazepin-3-yl]-3-(3-tolyl)urea or a pharmaceutically acceptable salt thereof.

8. The benzodiazepine derivative of claim 1 which is (+)-1-[2,3-Dihydro-1-(4'-methylphenacyl)-5-phenyl-1H-1,4-benzodiazepin-2-on-3-yl]-3-(3-methylphenyl)urea or a pharmaceutically acceptable salt thereof.

9. The benzodiazepine derivative of claim 1 which is (−)-1-[2,3-Dihydro-1-(4'-methylphenacyl)-5-phenyl-1H-1,4-benzodiazepin-2-on-3-yl]-3-(3-methylphenyl)urea or a pharmaceutically acceptable salt thereof.

10. A medicinal composition comprising a novel benzodiazepine derivative or a salt thereof as defined in claim 1 and a pharmaceutically acceptable carrier.

11. A benzodiazepine compound represented by the formula:

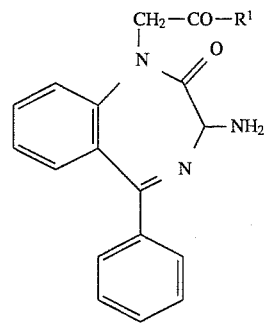

wherein $R^1$ is an aryl group, or an aromatic heterocyclic radical of a 5-membered monocyclic, a 6-membered monocyclic or a 5- and 6-membered bicyclic structure, which may optionally be substituted; and $R^2$ is an aryl group which may optionally be substituted.

* * * * *